(12) United States Patent
Sesha

(10) Patent No.: US 8,551,524 B2
(45) Date of Patent: Oct. 8, 2013

(54) ANTI-DIABETIC COMBINATIONS

(75) Inventor: Ramesh Sesha, West Windsor, NJ (US)

(73) Assignee: IYCUS, LLC, Princeton Junction, NJ (US)

( * ) Notice: Subject to any disclaimer, the term of this patent is extended or adjusted under 35 U.S.C. 154(b) by 471 days.

(21) Appl. No.: 12/560,292

(22) Filed: Sep. 15, 2009

(65) Prior Publication Data

US 2010/0074950 A1   Mar. 25, 2010

Related U.S. Application Data

(63) Continuation-in-part of application No. PCT/US2008/057054, filed on Mar. 14, 2007.

(51) Int. Cl.
| | |
|---|---|
| A61K 9/30 | (2006.01) |
| A01N 43/54 | (2006.01) |
| A01N 43/36 | (2006.01) |
| A01N 43/38 | (2006.01) |
| A01N 37/52 | (2006.01) |
| A01N 43/58 | (2006.01) |

(52) U.S. Cl.
USPC ........... 424/475; 514/274; 514/423; 514/412; 514/635; 514/249

(58) Field of Classification Search
USPC ........... 424/475; 514/274, 423, 412, 635, 249
See application file for complete search history.

(56) References Cited

U.S. PATENT DOCUMENTS

| | | | |
|---|---|---|---|
| 3,174,901 A | 3/1965 | Sterne | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,034,758 A | 7/1977 | Theeuwes | |
| 4,036,228 A | 7/1977 | Theeuwes | |
| 4,077,407 A | 3/1978 | Theeuwes et al. | |
| 4,522,625 A | 6/1985 | Edgren | |
| 4,612,008 A | 9/1986 | Wong et al. | |
| 4,783,337 A | 11/1988 | Wong et al. | |
| 5,071,607 A | 12/1991 | Ayer et al. | |
| 6,011,049 A | 1/2000 | Whitcomb | |
| 6,099,859 A | 8/2000 | Cheng et al. | |
| 6,110,949 A | 8/2000 | Villhauer | |
| 6,153,632 A | 11/2000 | Rieveley | |
| 6,166,063 A | 12/2000 | Villhauer | |
| 6,303,661 B1 | 10/2001 | Denmuth et al. | |
| 6,340,475 B2 | 1/2002 | Shell et al. | |
| 6,395,767 B2 | 5/2002 | Robl et al. | |
| 6,403,121 B1 | 6/2002 | Adjei et al. | |
| 6,451,342 B2 | 9/2002 | Adjei et al. | |
| 6,475,521 B1 | 11/2002 | Timmins et al. | |
| 6,524,621 B2 | 2/2003 | Adjei et al. | |
| 6,676,966 B1 | 1/2004 | Odidi et al. | |
| 7,125,873 B2 | 10/2006 | Edmondson et al. | |
| 7,241,756 B2 | 7/2007 | Arch et al. | |
| 7,368,421 B2 | 5/2008 | Demuth et al. | |
| 7,368,576 B2 | 5/2008 | von Hoersten et al. | |
| 7,371,759 B2 | 5/2008 | Ahmad et al. | |
| 7,390,809 B2 | 6/2008 | Kim et al. | |
| 7,393,838 B2 | 7/2008 | Fujikura et al. | |
| 7,414,072 B2 | 8/2008 | Sato et al. | |
| 2004/0106660 A1 | 6/2004 | Kositprapa et al. | |
| 2005/0163842 A1 | 7/2005 | Boehm et al. | |
| 2005/0249809 A1 | 11/2005 | Lodin et al. | |
| 2005/0266080 A1 | 12/2005 | Desai et al. | |
| 2006/0141128 A1 | 6/2006 | Ohkouchi et al. | |
| 2006/0160736 A1 | 7/2006 | Nadler | |
| 2007/0098781 A1 | 5/2007 | Loeffler et al. | |
| 2007/0172525 A1 | 7/2007 | Sesha | |
| 2008/0064701 A1 | 3/2008 | Sesha | |
| 2009/0105265 A1 | 4/2009 | Kamali et al. | |

FOREIGN PATENT DOCUMENTS

| | | |
|---|---|---|
| EP | 0749751 | 12/1996 |
| EP | 1552832 | 7/2005 |
| WO | WO 98/19998 | 5/1998 |
| WO | WO 00/34241 | 6/2000 |
| WO | WO 01/03594 | 1/2001 |
| WO | WO 03/004498 A1 | 1/2003 |
| WO | WO 2004/045608 | 6/2004 |
| WO | WO 2004/045622 | 6/2004 |
| WO | WO 2004/101514 A1 | 11/2004 |
| WO | WO 2004/110422 | 12/2004 |
| WO | WO 2005/073186 A1 | 8/2005 |
| WO | WO 2006036007 A2 * | 4/2006 |
| WO | WO 2006/047248 | 5/2006 |
| WO | WO 2006/082523 | 8/2006 |

(Continued)

OTHER PUBLICATIONS

FIP Guidelines for Dissolution Testing of Solid Oral Products, Joint Report of the Section for Official Laboratories and Medicines Control Services and the Section of Industrial Pharmacists of the F.I.P., available at http://www.fip.org/uploads/database_file.php?id=260 &table_id= (1997).*

Guidance for Industry: Dissolution Testing of Immediate Release Solid Oral Dosage Forms, U.S. Department of Health and Human Services, Food and Drug Administration, Center for Drug Evaluation and Research, available at http://www.fda.gov/downloads/Drugs/GuidanceComplianceRegulatoryInformation/Guidances/UCM070237.pdf (1997).*

PCT/US2008/057054 International Search Report mailed Mar. 14, 2008.

(Continued)

*Primary Examiner* — Frederick Krass
*Assistant Examiner* — Dennis J Parad
(74) *Attorney, Agent, or Firm* — Prout International IP, LLC

(57) ABSTRACT

A pharmaceutical composition comprising a dipeptidyl peptidase IV inhibitor and a slow release biguanide is provided. A method for treating diabetes in a patient in need thereof including administering an anti-diabetic combination comprising a DPP inhibitor and a slow release biguanide is also provided.

11 Claims, 24 Drawing Sheets

(56) References Cited

FOREIGN PATENT DOCUMENTS

| WO | WO 2006/115289 | 11/2006 |
|---|---|---|
| WO | WO 2007/078726 | 7/2007 |
| WO | WO 2008/113000 | 9/2008 |

OTHER PUBLICATIONS

Ahren B. et al. The DDP-4 inhibitor, LAF 237, improves glycemic control in Patients with type 2 diabetes (T2DM) inadequately treated with metformin [Online]URL: http://test.attendeeinteractive.com/shows/ada0401/index.cfm?fuseaction=Locator.SearchAbstracts>.

Ahren B. et al., Improved meal-related beta-cell function and insulin sensitivity by the dipeptidyl peptidase-IV inhibitor vildagliptin in metformin-treated patients with type 2 diabetes over 1 year. Diabetes Care, vol. 28, No. 8 pp. 1936-1940 (2005).

Aschner, P. et al., Effect of the dipeptidyl peptidase-4 inhibitor sitagliptin as monotherapy on glycemic control in patients with type 2 diabetes. Diabetes Care. 2006 vol. 29, 2632-2637., (2006).

Chahal, H. et al. Gliptins: a new class of oral hypoglycaemic agent, QJ Med. vol. 100, pp. 671-677 (2007).

Charbonnel, B. et al., Efficacy and safety of the dipeptidyl peptidase-4 inhibitor. sitagliptin added to ongoing metformin therapy in patients with type 2 diabetes inadequately controlled with metformin alone. Diabetes Care. 2006, vol. 29, 2638-2643, (2006).

Chyan, Y. Dipeptidyl Peptidase-IV Inhibitors: an evolving Treatment for Type 2 Diabetes from the Incretin Concept, Recent Patents on Endocrine, metabolic & Immune Drug Discovery. vol. 1, pp. 15-24, (2007).

Deacon, C., Perspectives in Diabetes—Therapeutic Strategies Based on Glucagon—Like Peptide 1, Diabetes. vol. 53 pp. 2181-2189, (2004).

Karttunen et al., The pharmacokinetics of metformin : a comparison of the properties of a rapid-release and a sustained-release preparation, Int. J. Clin. Pharmacology, Therapy and Toxicology. 1983, vol. 21, No. 1, pp. 31-36., (1983).

Mest, H.J. et al., Dipeptidyl peptidase inhibitors as new drugs for the treatment of type 2 diabetes, Diabetologia. vol. 48, pp. 616-620, (2005).

Noel, D. S., Kinetic study of normal and sustained release dosage forms of metformin in normal subjects, Journal of International Biomedical Information and Data, 1980vol. 1, pp. 9 to- 20., (1980).

Pentikainen, P. J., Bioavailability of Metformin. Comparison of solution, rapidly dissolving tablet, and three sustained release products. International Journal of Clinical Pharmacology, Therapy and Toxicology,1986 vol. 24, 213-220., (1986).

Raz, I. et al., Efficacy and safety of the dipeptidyl peptidase-4 inhibitor sitagliptin as monotherapy in patients with type 2 diabetes mellitus. Diabetologia. 2006, vol. 49, 2564-2571., (2006).

Rosenstock, J. et al. Efficacy and safety of the dipeptidyl peptidase-4 inhibitor sitagliptin added to ongoing pioglitazone therapy in patients with type 2 diabetes: a 24-week, multicenter, randomized, double-blind, placebo-controlled, parallel-group study. Clin. Ther.2006, vol. 28, 1556-1568., (2006).

Rotella, Miniperspectives: Advances in Type 2 Diabetes Therapy, J. Med Chem., vol. 47, No. 17, pp. 4111-4112, (2004).

Vidon, N., Chaussade, S., Noel, M., Franchisseur, C., Huchet, B., Bernier, J. J.,et al., Metformin in the digestive tract. Diabetes Research and Clinical Practice. 1988 vol. 4, 223-239., (1988).

Weber, A.E., Dipeptidyl Peptidase IV Inhibitors for the Treatment of Diabetes, J. Med. Chem., vol. 47, pp. 4135-4141, (2004).

www.rxwiki.com/index.php?title-Buformin 2008.

www.naturdoctor.com/Chapters/Drugs/Phenformin.html 2007.

\* cited by examiner

FIGURE 1, Fasting Plasma Glucose-Treatment F

FIGURE 2: HbA1c

FIGURE 3, Monotherapy v. Treatment F

ANTI-DIABETIC COMBINATIONS

RELATED APPLICATIONS

This application is a continuation-in-part under 35 U.S.C. 111(a) of International Application No. PCT/US2008/057054, filed on Mar. 14, 2008, and published in English as WO 2008/0113000 on Sep. 18, 2008, which claims priority to U.S. pat. application Ser. No. 11/724,486, filed Mar. 15, 2007 and U.S. patent application Ser. No. 11/789,080 filed Apr. 24, 2007, the disclosures of which are incorporated herein by reference in their entirety.

BACKGROUND

Type II diabetes mellitus (T2DM) is a progressive metabolic disorder with diverse pathologic manifestations and is often associated with lipid metabolism and glycometabolic disorders. The long-term effects of diabetes result from its vascular complications, e.g., the microvascular complications of retinopathy, neuropathy and nephropathy, and the macrovascular complications of cardiovascular, cerebrovascular and peripheral vascular diseases. Initially, diet and exercise is the mainstay of treatment of type II diabetes. However, this is often followed by administration of oral hypoglycemic agents. Exemplary drugs useful for managing type II diabetes and its precursor syndromes such as insulin resistance include classes of compounds, such as, biguanides, glitazones, sulfonylureas, thiazolidinediones α-glycosidase inhibitors, meglitinides and dipeptidyl peptidase IV inhibitors (DPP4 inhibitors).

Presently, dipeptidyl peptidase IV inhibitors, biguanides, glitazones and sulfonylureas are commercially available in the form of tablets of the individual drugs, either in immediate release (IR) formulations or in controlled release (CR) formulations. These are usually administered orally to patients in need thereof, using protocols calling for the administration of the individual ingredient.

Insulin resistance and reduced insulin secretion are two abnormalities that can occur in type 2 diabetic patients. Therefore, reducing insulin resistance or increasing insulin sensitivity and augmenting insulin secretion from the pancreatic beta cells are two major treatment approaches. The tissues most commonly resistant to actions of insulin are liver, skeletal muscles, and adipose tissues. Therefore, combination treatment strategies directed towards improving the insulin sensitivity of these major tissues can help in overall enhancement of insulin sensitivity.

In some cases, physicians have been initiating therapy for T2DM using at least two drugs to obviate the mono-therapy difficulties that can accompany prolonged use of metformin. Metformin mono-therapy typically has been used as a first line treatment in diabetic patients. This treatment may be supplemented with other drugs if secondary failure of the therapy arises. The addition of a second drug, e.g., dipeptidyl peptidase IV inhibitor, glitazones or a sulfonylurea to the concurrent treatment can provide a balance of stimulated release of insulin while ameliorating insulin resistance. This may provide an optimal level of glycemic control that is currently unattainable using either medication alone. However, requiring a patient to take multiple medications such as these for the prophylaxis or treatment of diseases can result in patient inconvenience and lead to non-compliance of the prescribed dosage regimen. The ease of using single composition for multiple medications as opposed to separate administration of the individual medications has long been recognized in the practice of medicine. Such a composition can provide a therapeutic advantage for the benefit of the patient and the clinician. Further, such a composition can provide both increased convenience and improved patient compliance resulting form the avoidance of missed doses through patient forgetfulness.

Pharmaceutical dosage forms containing combinations of anti-diabetic drugs are known from for example, EPO 0 749 751 discloses pharmaceutical compositions comprising an insulin sensitivity enhancer, such as a thiazolidinedione compound, in combination with other anti-diabetic compounds. More specifically, EPO 0 749 751 discloses pioglitazone as a insulin sensitivity enhancer, which can be combined with other anti-diabetics such as metformin, phenformin or buformin, and further that these drugs can be associated (mixed or coated) with conventional excipients to provide taste masking or provide a sustained or slow release. U.S. Pat. No. 6,011,049 discloses a combination of antihyperglycemic drugs and thiazolidinedione derivatives. This patent discloses a pharmaceutical composition having pioglitazone or trolitazone and metformin in slow release forms such as osmotic pumps or skin patches. Other combinations of antihyperglycemic drugs and thiazolidinedione derivatives can be found in U.S. Pat. Nos. 6,524,621; 6,475,521; 6,451,342 and 6,153,632 and PCT patent applications WO 01/3594 and WO 01/3594. U.S. Pat. No. 7,125,873 describes pharmaceutical composition comprising a dipeptidyl peptidase IV inhibitor like Sitagliptin with other anti-diabetic drugs such as biguanide and PPAR agonists. U.S. Pat. Application No. 2009/0105265 discloses pharmaceutical compositions comprising fixed-dose combinations of a dipeptidyl peptidase-4 inhibitor and metformin, methods of preparing such pharmaceutical compositions, and methods of treating Type 2 diabetes with such pharmaceutical compositions.

There is a need for pharmaceutical compositions comprising a dipeptidyl peptidase IV inhibitor and a slow release biguanide. Further the invention provides a method of administering the combination of a slow release biguanide and a dipeptidyl peptidase IV inhibitor that provides the advantages discussed above. It is an additional object of the present invention to provide a dosage form that can provide delivery of a DPP inhibitor and a biguanide wherein the peak plasma levels of the biguanide compound is approximately 8-12 hours after administration and peak plasma levels of a DPP IV inhibitor is approximately 1-4 hours after dosing. DPP IV inhibitor and Metformin combinations have been reported to cause diarrhea; gas; headache; indigestion; nausea; sore throat; stomach upset; stuffy or runny nose; vomiting; weakness. The extent of common adverse drug reactions reported include diarrhea (2.4%); gas (3.2%), stomach upset (2.6%), hypoglycemia (0.6% to 12.2%), headache (1.1% to 5.9%), nasopharyngitis (5.2% to 6.3%), upper respiratory infection (4.5% to 6.3%), etc. Thus there is a need for pharmaceutical compositions that alleviate or minimize these side effects.

SUMMARY

The present invention provides in one aspect pharmaceutical compositions comprising a dipeptidyl peptidase IV (DPP4) inhibitor and a slow release biguanide. The compositions can provide continuous and non-pulsating therapeutic levels of said biguanide to an mammal e.g., a human, in need of such treatment over about an eight hour to about a twenty-four hour period. Examples of dipeptidyl peptidase IV (DPP4) inhibitors, include Sitagliptin, Vildagliptin or Saxagliptin, Alogliptin, Dutogliptin. Examples of biguanides include metformin, phenformin, or buformin.

In another aspect the invention provides a method for administering a composition comprising of a slow release biguanide and a dipeptidyl peptidase IV inhibitor to a patient in need thereof. The composition can include dipeptidyl peptidase IV (DPP4) inhibitors, such as Sitagliptin, Vildagliptin or Saxagliptin, Alogliptin, Dutogliptin and biguanides such as metformin, phenformin, or buformin.

In another aspect the invention provides a method for treating diabetes comprising administering, to a patient in need thereof. The composition can include dipeptidyl peptidase IV (DPP4) inhibitors, such as Sitagliptin, Vildagliptin or Saxagliptin, Alogliptin, Dutogliptin and biguanides such as metformin, phenformin, or buformin.

In another aspect, the present invention provides a dosage form that can deliver a dipeptidyl peptidase IV inhibitor and a biguanide wherein the peak plasma levels of the biguanide compound is approximately 8-12 hours after administration and peak plasma levels of a DPP IV inhibitor is approximately 1-4 hours after dosing.

In another aspect, the invention provides a pharmaceutically acceptable salt thereof of the biguanides or dipeptidyl peptidase IV inhibitors.

In yet another aspect, the invention provides a dipeptidyl peptidase IV inhibitor and a slow release the biguanide wherein the active agents are administered in suboptimal dosages.

In yet another aspect, the invention provides a dipeptidyl peptidase IV inhibitor and a slow release the biguanide wherein the active agents are administered in amounts and for a sufficient time to produce a synergistic effect.

In yet another aspect, the invention provides pharmaceutical compositions comprising pharmaceutically acceptable salts of the dipeptidyl peptidase IV (DPP IV) inhibitor and the biguanide.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
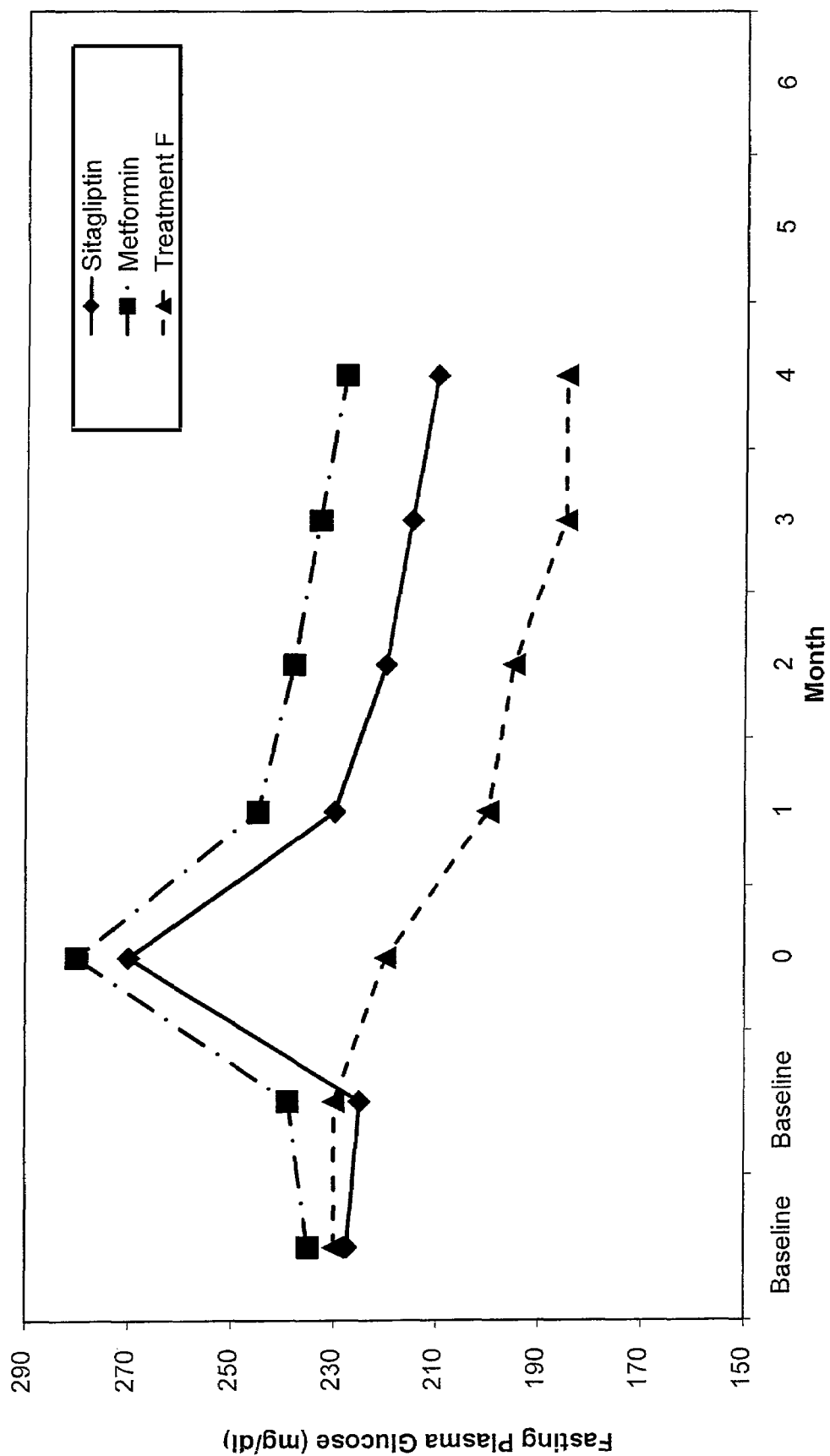
FIG. 1: Illustrates a change in fasting plasma glucose (FPG) (+/−) SEM during sitagliptin, metformin hydrochloride monotherapy and Treatment F comprising sitagliptin phosphate and slow release metformin hydrochloride fixed dose combination.

The terms "a," "an," "the," "at least one," and "one or more" are used interchangeably. Thus, for example, a composition that comprises "an" element means one element or more than one element.

"Sulfonylurea" refers to drugs such as glipizide, glimiperide, glyburide, glibornuride, glisoxepide, gliclazide acetohexamide, chlorpropamide, tolazamide, and tolbutamide, among others that control or manage non-insulin-dependent diabetes mellitus (NIDDM) by stimulating the release of endogenous insulin from the beta cells of the pancreas.

"Thiazolidinediones" includes compounds such as Troglitazone, Pioglitazone, Rosiglitazone, Ciglitazone, Isaglitazone, Darglitazone, zorglitazone, Englitazone, Balaglitazone and the like. Glitazones are believed to act by increasing the sensitivity of insulin receptors in the body and decreasing peripheral insulin resistance. Glitazones, such as pioglitazone, stimulate adipogenesis and reduce plasma triglyceride and free fatty acid concentrations. These compounds are believed to enhance insulin action at the cellular level but do not stimulate insulin release, or mimic its action.

"α-Glycosidase Inhibitors" include compounds such as α-glucosidase inhibitors, acarbose, miglitol and the like. Both drugs are believed to block the enzymes that digest the starches in the small intestine. This action is believed to cause a slower and lower rise of blood glucose through the day, but mainly right after meals. Neither acarbose nor miglitol causes hypoglycemia when it is the only diabetes medicine. Additional compounds in this class include acarbose, miglitol, voglibose, emiglitate, and the like.

"Meglitinides" refers to a class of drugs that includes Repaglinide, Nateglinide. Meglitinides are non-sulfonylureal insulin secretagogues that are believed to lower blood sugar levels by stimulating the release of insulin from the pancreas in response to glucose (from food).

The term "glitazones" refers to compounds such as, rosiglitazone, troglitazone and pioglitazone, and the like, which act by increasing the sensitivity of insulin receptors in the body and decreasing peripheral insulin resistance. Glitazones, e.g., pioglitazone, stimulate adipogenesis and reduce plasma triglyceride and free fatty acid concentrations. These enhance insulin action at the cellular level but do not stimulate insulin release, or mimic its action.

The term "diabetes and diabetes related diseases" refers to the diseases such as type 1 diabetes, type 2 diabetes, hyperglycemia, type 1.5 diabetes, latent autoimmune diabetes (e.g., in adults), maturity onset diabetes, beta-cell apoptosis, hemochromatosis induced diabetes, impaired glucose tolerance, metabolic syndrome X, insulin resistance, cystic fibrosis related diabetes, polycystic ovarian syndrome, gestational diabetes, obesity, dyslipidemia, diabetic dyslipidemia, hyperlipidemia, hypertriglyceridemia, hyperlipoproteinemia, hypercholesterolemia, hypertension, essential hypertension, acute hypertensive emergency, arteriosclerosis, atherosclerosis, intermittent claudication (atherosclerosis oblilterens), cardiovascular disease, cardiomyopathy, cardiac hypertrophy, left ventricular hypertrophy, coronary artery disease, early coronary artery disease, heart insufficiency, exercise tolerance, chronic heart failure, mild chronic heart failure, arrhythmia, cardiac dysrythmia, syncopy, heart attack, myocardial infarction, Q-wave myocardial infarction, stroke, acute coronary syndrome, angina pectoris, unstable angina, cardiac bypass reocclusion, diastolic dysfunction, systolic dysfunction, non-Q-wave cardiac necrosis, catabolic changes after surgery, acute pancreatitis, irritable bowel syndrome, diabetic retinopathy, background retinopathy, preproliferative retinopathy, proliferative retinopathy, macular edema, cataracts, nephropathy, diabetic nephropathy, microalbuminuria, macroalbuminuria, neuropathy, diabetic neuropathy, distal symmetrical sensorimotor polyneuropathy, and diabetic autonomic neuropathy.

The term "co-administration" means administration of the two compounds (e.g., drugs) to a patient within a period of one day. The term includes separate administration of two medicaments (drugs) each containing one of the compounds as well as simultaneous administration where the two compounds may be combined in one formulation or administered in two separate formulations.

A "therapeutically effective amount" of a compound is that amount of compound which is sufficient to provide a beneficial effect to the subject to which the compound is administered. For example, a therapeutically effective amount of an biguanide is an amount that can control of blood glucose by inhibiting hepatic glucose production.

The term "medicament" means a pharmaceutical composition suitable for administration of the pharmaceutically active compound (drug) to a patient.

The term "pharmaceutically-acceptable salt" refers to salts that retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto. The preparation of the salts and suitable acids or bases are known in the art.

The term "suboptimal dosage" means a dosage which is below the optimal dosage for that compound when used in single-compound therapy.

The term "additive effect" means the effect resulting from the sum of the effects obtained from the individual compounds is equal to the sum of their individual effects in isolation.

The term "synergistic effect" means an effect which is greater than the additive effect which results from the sum of the effects of the two individual compounds.

The term "treating or treatment" means the management and care of a patient having developed the disease, condition or disorder and includes prophylaxis of the specific disorder or condition, or alleviation of the symptoms associated with a specific disorder or condition or preventing or eliminating said symptoms. Treatment includes the administration of the active compounds to eliminate or control the disease, condition or disorder as well as to alleviate the symptoms or complications associated with the disease, condition or disorder.

The term "prevention of a disease" refers to the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term "slow-release" refers to a formulation that is other than an immediate release, e.g., wherein the release of the active ingredient is slow in nature. This includes various terms used interchangeably in the pharmaceutical context such as extended release, delayed release, sustained release, controlled release, timed release, specific release, targeted release etc. Examples of a slow release include a core where a biguanide is released at a rate where the peak plasma levels of the biguanide compound is achieved approximately 8-22 hours after administration.

The term "candidate for sustained release" encompasses all the characteristics of a drug which make it a candidate for formulating it into an extended release fashion like a short elimination half life and consequent dosing of more than once a day, a single dose product given in an extended fashion to achieve better clinical results and avoid side effects associated with an immediate release, etc.

The term "pharmaceutically acceptable derivative" means various pharmaceutical equivalent isomers, enantiomers, complexes, salts, hydrates, polymorphs, esters, etc.

The term "seal coat" refers to a coating that does not contain an active pharmaceutical ingredient and that typically will rapidly disperses or dissolves in water.

"Instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

Exemplary biguanides include drugs that are useful in controlling or managing non-insulin-dependent diabetes mellitus (NIDDM). Non-limiting examples of biguanides include metformin, phenformin or buformin and the like and pharmaceutically acceptable salts, or isomers thereof.

Exemplary dipeptidyl peptidase IV (DPP4) inhibitors include drugs that are useful for controlling or managing non-insulin-dependent diabetes mellitus (NIDDM). Non-limiting examples of dipeptidyl peptidase IV (DPP4) inhibitors include, Sitagliptin, Saxagliptin, Vildagliptin and other molecular entities such as SYR 522 (pyrimidine derivatives such as Alogliptin), PHX1149 (Dutogliptin), GRC-8200 (tricyclic derivatives), SSR162369 (bicyclic 8-pyrrolidinoxanthine) derivatives that inhibit dipeptidyl peptidase IV protease in a mammal. A preferred dipeptidyl peptidase IV inhibitor is Sitagliptin, or a pharmaceutically acceptable salt thereof.

Typical combinations include sitagliptin with a slow release metformin core. Another preferred combination is vildagliptin with a slow release metformin core. Yet another preferred combination is saxagliptin with slow release metformin core. Yet another preferred combination is alogliptin with slow release metformin core. Yet another preferred combination is dutogliptin with slow release metformin core. These combinations can produce better than expected therapeutic benefit in the treatment of diabetes and diabetes related diseases.

The invention provides an anti-diabetic combination for the treatment of diabetes and diabetes related diseases. A dipeptidyl peptidase IV inhibitor is used in combination with a slow release biguanide, to treat diabetes and diabetes related diseases and to improve glycemic control in patients in need of treatment.

Further, the invention provides a pharmaceutical composition having a biguanide as a controlled or sustained release component and a dipeptidyl peptidase IV inhibitor as an immediate release component, wherein at least 85% of the total amount of the DPP IV inhibitor is released from the dosage form within 120 minutes or less. Preferably, at least 95% of the dipeptidyl peptidase IV inhibitor is released within 90 minutes when tested in a USP type 1 apparatus, at pH 2.0 in a HCl-0.3M KCl buffer solution.

In another aspect of the invention, the active compounds can be employed individually, or can be combined in a single formulation, for example as a tablet, capsule, syrup, solution, as well as controlled release formulations. In a preferred embodiment, the dipeptidyl peptidase IV inhibitor and a slow release biguanide are formulated individually and administered in the same manner that each is normally used clinically.

In another aspect the invention provides a pharmaceutical composition or dosage form comprising a slow release biguanide as the first active ingredient and a dipeptidyl peptidase IV inhibitor as the second active ingredient. A preferred biguanide metformin or a pharmaceutically acceptable salt thereof. The metformin is preferably delivered in a controlled release manner (slow release), e.g., from a tablet core. An exemplary core is an osmotic tablet core with or without a gelling or swelling polymer. The tablet core includes the biguanide and can include at least one pharmaceutically acceptable excipient. An example of a biguanide tablet core includes the biguanide, a binding agent and an absorption enhancer, and the tablet core is preferably coated with a polymeric coating to form a membrane around the tablet and drilled to create one passageway on each side of the membrane. The second active ingredient includes a dipeptidyl peptidase IV inhibitor or a pharmaceutically acceptable salt, and is preferably applied to the membrane of the tablet core and can provide either immediate or controlled release of the dipeptidyl peptidase IV inhibitor.

The compositions can optionally include an absorption enhancer, which can be any type of absorption enhancer commonly known in the art such as a fatty acid, a surfactant (anionic, cationic, amphoteric), a chelating agent, a bile salt and the like or mixture thereof. Non-limiting examples of absorption enhancers include lecithin, fatty acids such as capric acid, oleic acid, monoglycerides thereof and the like, surfactants such as sodium lauryl sulfate, sodium taurocholate and polysorbate 80 and the like, chelating agents such as citric acid, phytic acid, ethylenediamine tetra acetic acid (EDTA) and ethylene glycol-bis(.beta.-amino ethyl ether)-N, N,N,N-tetra acetic acid (EGTA) and the like. The core may include from 0 to about 20 weight % absorption enhancer based on the total weight of the core and preferably about 2% to about 10 weight % of the total weight of the core.

In one example, the core of is preferably formed by granulating a biguanide with a binding agent and compressing the granules with a lubricant and an absorption enhancer into a tablet. The core may also be formed either by dry granulating the core ingredients into a mixture and passing the mixture through a roller compactor and compressing the granules, with a lubricant, into tablets or by direct compression. The cores can also be prepared using other commonly known granulation procedures that are known in the art. For example other excipients such as lubricants, pigments or dyes known in the art may also be employed in the formulation of the subject invention.

A membrane or sustained release coating may be used to coat the core. Materials that are useful in forming a membrane or slow release coating are ethylcellulose, cellulose esters, cellulose diesters, cellulose triesters, cellulose ethers, cellulose ester-ether, cellulose acrylate, cellulose diacrylate, cellulose triacrylate, cellulose acetate, cellulose diacetate, cellulose triacetate, cellulose acetate propionate and cellulose acetate butyrate. Other suitable polymers are described in U.S. Pat. Nos. 3,845,770; 3,916,899; 4,008,719; 4,036,228 and 4,612,008. a preferred coating material is cellulose acetate, having an acetyl content of 39.3 to 40.3%, which is commercially available from Eastman Fine Chemicals.

Optionally a flux-enhancing agent can be included in the membrane or slow release coating. The flux enhancing agent can increase the volume of fluid imbibed into the core to enable the dosage form to dispense substantially all of the biguanide through the passage or the porous membrane. The flux-enhancing agent can be a water-soluble material or an enteric material. Non-limiting examples of flux enhancers include sodium chloride, potassium chloride, sucrose, sorbitol, mannitol, polyethylene glycols (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers (such as LUTROL F68, LUTROL F127, LUTROL F108 which are commercially available from BASF) or mixture thereof. A preferred flux-enhancing agent is PEG 400.

The flux enhancer may also be a water soluble drug such as metformin or a pharmaceutically acceptable salt, or the flux enhancer may be a drug that is soluble under intestinal conditions. If the flux enhancer is a drug, the present pharmaceutical composition has an added advantage of providing an immediate release of the drug selected as the flux enhancer. The flux enhancing agent can dissolve or leach from the membrane or sustained release coating to form channels in the membrane or sustained release coating which enables fluid to enter the core and dissolve the active ingredient. Preferably, the flux enhancing agent is from 0 to about 40% of the total weight of the coating, most preferably from about 2% to about 20 weight % of the total weight of the coating.

Excipients such as plasticizers may be used for preparing the membrane or slow release coating. Non-limiting examples of plasticizers include adipates, azelates, enzoates, citrates such as triethyl citrate, tri-n-butyl citrate, acetyl tri-n-butyl citrate, acetyltributylcitrate, acetyltriethylcitrate and the like, stearates, isoebucates, sebacates, and plasticizers described in the Encyclopedia of Polymer Science and Technology, Vol. 10 (1969), published by John Wiley & Sons. Preferred plasticizers include triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and the like. The exact amount of plasticizer used depends on the type of plasticizer. Typically, the plasticizer can be from 0 to about 25 weight % are used, and preferably about 2 to about 15 weight % based upon the total weight of the membrane or sustained release coating.

Generally, the membrane or slow release coating can comprise from about 1 to about 10 weight % and preferably about 2 to about 5 weight % based upon the total weight of the core and coating.

The membrane or sustained release coating surrounding the core further comprises a passage that can allow for controlled release of the drug from the core in a preferred embodiment. The term "passage" includes an aperture, orifice, bore, hole, weakened area or a credible element such as a gelatin plug that erodes to form an osmotic passage for the release of the biguanide from the dosage form. Exemplary passages are well known and described, e.g., in U.S. Pat. Nos. 3,845,770; 3,916,899; 4,034,758; 4,077,407; 4,783,337 and 5,071,607.

The present invention provides a combination that includes a dipeptidyl peptidase IV inhibitor that is independent of the biguanide. The dipeptidyl peptidase IV inhibitor is a second active ingredient and can be formulated to provide an immediate release of the inhibitor. In one example the dipeptidyl peptidase IV inhibitor can be applied in the form of a layer to a controlled or slow released core comprising the a biguanide as a layer using a binder and other conventional pharmaceutical excipients such as absorption enhancers, surfactants, plasticizers, antifoaming agents and combinations disclosed above. An absorption enhancer may be present in the dipeptidyl peptidase IV inhibitor layer in an amount up to about 30 weight % based on the total weight of the layer. A binding agent may be present in an amount up to about 150 weight % based on the weight of the dipeptidyl peptidase IV inhibitor.

The second active ingredient (immediate release formulation) can be incorporated into a single dosage form by coating a layer containing the active ingredient onto the membrane or slow release coating of the dosage form using conventional methods. Alternatively, the active ingredient may also be incorporated by any pharmaceutically acceptable method into a single dosage form with the first active ingredient. The incorporation of the second active ingredient may be performed, among others, by commonly used processes including drug layering, lamination, dry compression, deposition and printing.

When a dipeptidyl peptidase IV inhibitor is coated onto a membrane or slow release coating of an osmotic tablet core, the dipeptidyl peptidase IV inhibitor coating can be applied from a coating solution or suspension that employs an aqueous solvent, an organic solvent or a mixture of an aqueous and an organic solvent. Exemplary organic solvents include acetone, isopropyl alcohol, methanol, ethanol and the like. When a mixture of aqueous and organic solvents is employed, the weight ratio of water to organic solvent should be in the range from 98:2 to 2:98, preferably 50:50 to 2:98, more preferably 30:70 to 20:80 and most preferably from about 25:75 to about 20:80. When mixed solvent systems are employed, the amount of binder required for coating the dipeptidyl peptidase IV inhibitor onto the membrane or a slow release coating can be reduced. For example, successful coatings have been obtained from a mixed solvent system where the weight ratio of binder to dipeptidyl peptidase IV inhibitor is 1:9 to 1:11. Although acceptable coatings can be obtained when the dipeptidyl peptidase IV inhibitor coat is applied directly to the membrane or slow release coating, a preferred method is to first coat the membrane or slow release coating with a seal coat prior to the application of the dipeptidyl peptidase IV inhibitor coating.

In one example, the dipeptidyl peptidase IV inhibitor coating solution or suspension can include a surfactant and a pore forming agent such as sodium chloride, potassium chloride, sucrose, sorbitol, mannitol, polyethylene glycols (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers. In another example, the pharmaceutical composition of the present invention may also include an effective immediate release amount of the biguanide. The effective immediate release amount of biguanide can be coated onto the membrane or slow release coating of the dosage form or it may be incorporated into the membrane or slow release coating.

In addition, various diluents, excipients, lubricants, dyes, pigments, dispersants, etc., which are disclosed in Remington's Pharmaceutical Sciences (1995), may be used to optimize the above listed formulations of the subject invention.

Biguanides, such as metformin are commonly administered in dosage forms containing 500 mg, 750 mg, 850 mg, and 1000 mg. dipeptidyl peptidase IV inhibitors, for example sitagliptin, is commonly administered in dosage forms containing 25 mg, 50 mg and 100 mg. The present invention is intended to encompass the above listed therapeutic combinations, without providing a specific example of each possible combination of compounds and their respective dosage amounts.

The use of a binding agent in the core is optional. Exemplary binding agents include conventional pharmaceutically acceptable binders known in the art such as polyvinyl pyrrolidone, hydroxypropyl cellulose, hydroxyethyl cellulose, hydroxypropyl methylcellulose, ethylcellulose, polymethacrylate, polyvinylalcohol, waxes and the like or mixtures thereof. Preferred binding agents are water soluble materials such as polyvinyl pyrrolidone having a weight average molecular weight of 25,000 to 3,000,000. The binding agent may comprise approximately about 0 to about 40 weight % of the total weight of the core and preferably about 3% to about 15 weight % based on the total weight of the core.

Exemplary hydrophilic polymers include, but are not limited, to hydroxypropylmethylcellulose, hydroxypropylcellulose, sodium carboxymethylcellulose, carboxymethylcellulose calcium, ammonium alginate, sodium alginate, potassium alginate, calcium alginate, propylene glycol alginate, alginic acid, polyvinyl alcohol, povidone, carbomer, potassium pectate, potassium pectinate, and the like or mixtures thereof.

Exemplary extended release materials for use in the inner solid particulate phase or the outer solid continuous phase include one or more hydrophilic polymers, one or more hydrophobic polymers, or one or more other type hydrophobic materials, such as, for example, one or more waxes, fatty alcohols or fatty acid esters. The extended release material in the inner solid particulate phase may be the same as or different from an extended release material present in the outer solid continuous phase.

Exemplary hydrophobic polymers include, but are not limited, to ethyl cellulose, hydroxyethylcellulose, amino methacrylate copolymer (Eudragit RL™ or Eudragit RS™), methacrylic acid copolymers (Eudragit L™ or Eudragit S™), methacrylic acid-acrylic acid ethyl ester copolymer (Eudragit L 100-5™), methacrylic acid esters neutral copolymer (Eudragit NE 30D™), dimethylaminoethylmethacrylate-methacrylic acid esters copolymer (Eudragit E 100™), vinyl methyl ether/malefic anhydride copolymers, their salts and esters (Gantrez™) and the like or mixtures thereof.

Additional hydrophobic materials which can be employed in the inner solid particulate phase or outer solid continuous phase include, but are not limited, to waxes such as beeswax, carnauba wax, microcrystalline wax, and ozokerite; fatty alcohols such as cetostearyl alcohol, stearyl alcohol; cetyl alcohol myristyl alcohol etc; and fatty acid esters such as glyceryl monostearate, glycerol monooleate, acetylated monoglycerides, tristearin, tripalmitin, cetyl esters wax, glyceryl palmitostearate, glyceryl behenate, hydrogenated castor oil, and the like or mixtures thereof.

Exemplary gelling or swelling polymers include polymers that gel, swell or expand in the presence of water or biological fluids. Non-limiting examples of gelling or swelling polymers are high molecular weight hydroxypropyl methylcellulose (such as METHOCEL™, K100M, which is commercially available from Dow Chemical) and high molecular weight polyethylene oxides (such as POLYOX™ WSR 301, WSR 303 or WSR COAGULANT). Other gelling or swelling polymers are described in U.S. Pat. No. 4,522,625.

The dosage of each active agent (compound) that is administered can be determined the attending physician who would consider the severity of the disease, the frequency of administration, the particular agents and combinations utilized, and other factors routinely considered in a diabetic practice. Typically, the dipeptidyl peptidase IV inhibitors will normally be administered at doses from about 50 mg to about 200 mg per day, and more preferably from about 100 mg to about 200 mg per day. A preferred dipeptidyl peptidase IV inhibitor is sitagliptin, and it typically will be employed at doses from about 50 mg to about 300 mg per day. Slow release metformin hydrochloride can be administered at doses of about 300 mg to about 2000 mg per day. Metformin hydrochloride is commercially available in tablets which contain 500 mg, 750 mg and 1000 mg of active agent. The number and frequency of the dosages administered depends on the nature of the disease and the conditions of the patients but can be given up to two times a day or more.

The invention provides compositions of anti-diabetic combinations, for example, dipeptidyl peptidase IV inhibitor and a slow release biguanide, and a method of treating diabetes and controlling glycemic conditions including administering to a patient in need of such treatment an effective amount of a dipeptidyl peptidase IV inhibitor and a slow release biguanide. When the dipeptidyl peptidase IV inhibitor and a slow release biguanide are formulated together, the compositions can have from about 1 and to about 1000 mg of weight dipeptidyl peptidase IV inhibitor and about 100 to about 2000 mg of biguanide. For example, a typical two-way composition can include 50 mg of sitagliptin and 500 mg of metformin. Yet another typical two-way composition can include 50 mg of vildagliptin and 500 mg of metformin. Still yet another typical two-way composition can include 5 mg of saxagliptin and 500 mg of metformin. Still yet another typical two-way composition can include 50 mg of alogliptin and 500 mg of metformin. Still yet another typical two-way composition can include 50 mg of dutogliptin and 500 mg of metformin. The compositions may contain common excipients and carriers such as starch, sucrose, polymers, talc, gelatin, methylcellulose, magnesium stearate and the like or mixtures thereof. The compositions will typically be prepared for oral administration, for instance as tablets or capsules, but also may be in the form of aqueous suspensions or solutions, suppositories, slow release forms, for example employing an osmotic pump, skin patch, or the like.

The disclosed compositions include a kit comprising a composition including a dipeptidyl peptidase IV (DPP IV) inhibitor and a slow release biguanide and instructional material that describes administering the composition to a subject. This should be construed to include other embodiments of kits that are known to those skilled in the art, such as a kit comprising a (preferably sterile) solvent for dissolving or suspending the composition prior to administering the composition to subject. Preferably, the subject is a human.

Exemplary compositions of the pharmaceutical composition form, using Sitagliptin Phosphate can have the compositions described in Table 1:

TABLE 1

|  | Range percent | Preferred Range % |
|---|---|---|
| First Active Ingredient |  |  |
| Drug | 50-98% | 75-95% |
| Binder | 0.1-40% | 3-15% |
| Absorption Enhancer | 0-20% | 2-10% |
| Lubricant | 0-5% | 0.5-1% |
| Coat |  |  |
| Polymer | 50-99% | 75-95% |
| Flux Enhancer | 0-40% | 2-20% |
| Plasticizer | 0-25% | 2-15% |
| Second Active Ingredient |  |  |
| Drug | 0.1-20% | 1-10% |
| Binder | 0.1-20% | 1-15% |
| Surfactant | 0-20% | 0.1-15% |
| Pore Former | 0-25% | 0.1-15% |
| Polymer (Optional) | 0-30% | 0.1-20% |

The invention is now described with reference to the following Examples. Without further description, it is believed that one of ordinary skill in the art can, using the preceding description and the following illustrative examples, make and utilize the disclosed compositions. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

EXAMPLE 1

Preparation of Metformin Hydrochloride/Sitagliptin Phosphate Composition

A slow-release tablet containing 500 mg of metformin HCl and 50 mg sitagliptin phosphate is prepared using a three step process: 1) Granulation, 2) Tableting and 3) Membrane coating process. An optional seal coating may be applied to the core tablet. The specific steps are described below.

Granulation: Metformin hydrochloride was screened using a size reduction and screening equipment (Comil screener) and was further fluidized using a commercially available powder coater granulator (Glatt 60). It was sprayed with a povidone solution prepared in a steel tank using water as the solvent. The spraying was carried at about 2.5 bar pressure by varying the pump rate from 0-15 minutes for a target of 500 g/min. to achieve a target of about 1200 g/min. in the final phase. Granules were dried until an LOD of less than 2% and passed through a screener (Comil 1143/75).

Tableting: The coated metformin hydrochloride was mixed with sodium lauryl sulfate in a blender (Slant-Cone: 30 minutes). Magnesium stearate was screened and blended with the metformin hydrochloride—sodium lauryl sulfate mixture. The homogenized mixture was compressed into tablets using standard procedures. The metformin hydrochloride core tablets weighted from 650 mg to 800 mg with a frigidity of less than 1%.

Seal coating: Seal coating of the metformin core tablets was accomplished by spraying (O'Hara Lab Coat Pan Coater) a solution of either Opadry coating material. The spraying was conducted at a temperature of 46-47° C., atomization pressure of 40-60 psi at a spray rate of 180 grams per minute/three guns. The pan speed was at 4-8 rpm and air volume of 1000+/−100. The seal coated metformin hydrochloride had a theoretical coating of 2.5-5.0 weight %.

Membrane coating: Cellulose acetate was mixed with acetone to prepare a clear solution. Polyethylene glycol 400 was added this mixture and triacetin was added to the resulting solution. The seal coated metformin hydrochloride tablets were fluidized using a Glatt coater. The cellulose acetate solution was sprayed onto the fluidized seal coated metformin hydrochloride tablets at an atomization pressure of 2.5 bars, using an air volume of 1700 CFM, at spraying rate of about 450g/ml to achieve coating target of 1.3 weight %. The membrane coated tablets were dried sequentially at temperature of 21° C. and 40° C. An orifice was made on the membrane coated tablets using laser with an average diameter of 0.4 to 0.5 mm with micrometer ranging from 6 to 7 mm. Laser was operated with pulse width of 165+/−65 and a pulse delay of around 340+/−100 respectively.

Manufacturing process of sitagliptin phosphate coating The above prepared membrane coated metformin hydrochloride tablets were further seal coated with Opadry Clear (YS-1-7006) solution using standard coater such as an O'Hara pan coater, tip set at 4" at a spray rate of 25 mL/gun/min, exhaust temperature of around 45° C., an atomization pressure from 10-35 psi, at a pan speed of 5-8 rpm, using airflow 350 CFM. The sitagliptin coating solution was prepared carefully and slowly by dissolving Lutrol F-68 in water. Similarly the povidone K-30 in water solution was prepared separately and was mixed with spray dried lactose monohydrate. Following the addition of lactose, sitagliptin was first dispersed in the above prepared Lutrol solution with constant stirring and finally sodium starch glycolate was added into the coating solution. The sitagliptin coating was applied to the seal coated 500 mg metformin hydrochloride membrane coated tablets using the above mentioned coater at identical conditions. Over this 50 mg sitagliptin coated seal coated 500 mg metformin hydrochloride membrane coated tablets, color coating was done using similar coater and identical conditions mentioned above.

Finally, color coated tablets were dried and polished using Cindrella wax and the finished final tablets were packaged in a HDPE bottle with a suitable desiccant and subjected appropriate stability and clinical studies.

Table 2 illustrates a representative example of a pharmaceutical composition of a slow release composition having a biguanide and a DPP inhibitor. The pharmaceutical composition used was 500 mg metformin hydrochloride and 50 mg of Sitagliptin Phosphate.

TABLE 2

|  | Amount mg/tablet |
|---|---|
| First Active Ingredient |  |
| Metformin HCl | 500.0 |
| Povidone K 301 USP | 30.0 |
| Sodium Lauryl Sulfate | 26.0 |
| Magnesium Stearate | 2.8 |
| Seal Coat |  |
| Opadry Clear (YS 1-7006) | 24.0 |
| Semi permeable coat |  |
| Cellulose Acetate (398-10) NF | 7.6 |
| Triacetin | 0.5 |
| PEG 400 | 0.9 |
| Seal coat |  |
| Opadry Clear (YS 1-7006) | 5.0 |
| Second Active Ingredient |  |
| Sitagliptin Phosphate | 50.0 |
| Povidone K 30 USP | 1.5 |
| Lactose Monohydrate | 35.0 |
| Sodium starch Glycolate | 12.5 |
| Poloxamer 188 | 6.0 |
| HPMC | 2.5 |
| PEG 8000 | 0.4 |
| Titanium Dioxide | 0.4 |
| Wax | 0.2 |

The dosage forms prepared above exhibit the dissolution profile illustrate in Table 3 when tested in a USP Type 2 apparatus at 75 rpm in 900 ml of simulated intestinal fluid (pH 7.5 phosphate buffer) and at 37° C.

TABLE 3

| Dissolution Profile | | |
|---|---|---|
| Time hours | Percent Release | Range |
| Biguanide | | |
| 2 | 0-25% | 0-15% |
| 4 | 10-45% | 20-40% |
| 8 | 30-90% | 45-90% |
| 12 | >50% | >60% |
| 16 | >60% | >60% |
| 20 | >70% | >70% |

TABLE 3-continued

| Dissolution Profile | | |
|---|---|---|
| Time hours | Percent Release | Range |
| DPP4 Inhibitor | | |
| 1 | >85% | >85% |

The selection of the excipients for use in the dipeptidyl peptidase IV ingredient layer of the dosage form can greatly affect the release characteristics, potency and stability of the dipeptidyl peptidase IV inhibitor. Therefore, in an alternate example, the composition of the dipeptidyl peptidase IV inhibitor component of the present invention should be selected so that at least about 85%, preferably at least about 90% and most preferably at least about 95% of the dipeptidyl peptidase IV inhibitor is released from the dosage form within 120 minutes, preferably within 90 minutes and most preferably within 60 minutes when tested according to the United States Pharmacopeia (USP) 26, with Apparatus 1 at 100 rpm, 37' C and 900 ml of 0.3 M KCl—HCl Buffer, pH 2.0.

The excipients for use in the dipeptidyl peptidase IV inhibitor layer of the dosage form are selected so that the total dipeptidyl peptidase IV inhibitor related compounds or impurities in the final dosage form are less than about 0.6 weight %, preferably less than about 0.5 weight % and most preferably less than about 0.25 weight % and each individual dipeptidyl peptidase IV inhibitor related compound or impurity in the final dosage form is less than about 0.25%, preferably less than about 0.2 weight % and most preferably less than about 0.1 weight %. The DPP inhibitor related compounds or impurities in the final dosage form are determined by High Performance Liquid Chromatography (HPLC) using a YMC-ODS-AQ, 5 μm, 120 Å, 4.6 times 250 mm or equivalent column, a 0.1 M ammonium acetate buffer:acetonitrile:glacial acetic acid (25:25:1) mobile phase, about a 40 μL injection volume, 0.7 mL/min flow rate, 25° C. column temperature and 269 nm wavelength for the UV detector.

EXAMPLE 2

A pharmaceutical composition comprising sitagliptin phosphate 100 mg and slow release metformin hydrochloride 1000 mg was manufactured as described in Example 1.

Table 4 shows the representative example of a pharmaceutical composition of a slow release composition having a biguanide and a DPP IV inhibitor. The pharmaceutical composition used was 1000 mg metformin hydrochloride and 100 mg of Sitagliptin Phosphate.

TABLE 4

|  | Amount mg/tablet |
|---|---|
| First Active Ingredient |  |
| Metformin HCl | 1000.0 |
| Povidone K 301 USP | 78.0 |
| Sodium Lauryl Sulfate | 51.7 |
| Magnesium Stearate | 5.7 |
| Seal Coat |  |
| Opadry Clear (YS 1-7006) | 47.0 |
| Semi permeable coat |  |
| Cellulose Acetate (398-10) NF | 15.5 |
| Triacetin | 0.9 |
| PEG 400 | 1.8 |

TABLE 4-continued

| | Amount mg/tablet |
|---|---|
| Seal coat | |
| Opadry Clear (YS 1-7006) | 9.0 |
| Second Active Ingredient | |
| Sitagliptin Phosphate | 100.0 |
| Povidone K 30 USP | 3.0 |
| Lactose Monohydrate | 70.0 |
| Sodium starch Glycolate | 25.0 |
| Poloxamer 188 | 12.0 |
| HPMC | 5.0 |
| PEG 8000 | 0.8 |
| Titanium Dioxide | 0.8 |
| Wax | 0.4 |

The following combinations were tested in vivo each in a cross over study with the combination of Glucophage 1000 mg (commercially available metformin XR 1000 mg) and Januvia 100 mg (commercially available sitagliptin phosphate 100 mg). The in vivo test employed 14 healthy volunteers and each dosed after evening meal.

The Pharmacokinetic parameters of metformin hydrochloride and sitagliptin phosphate are listed in Table 5 and Table 6 respectively

TABLE 5

Metformin Parameter

| Combination drug/day | Mean AUC0-12 (ng·hr/ML) | Mean $C_{max}$ (ng/ML) | Mean $T_{max}$ hr | AUC Ratio (Test/BID) | $C_{max}$ (Test/BID) |
|---|---|---|---|---|---|
| 2 Glucophage 500 mg + 2 Januvia 50 mg (BID) | 10246 | 1454 | 3 | 1 | 1 |
| Fortamet 1000 mg + Januvia 100 mg | 11900 | 1424 | 6.3 | 1.16 | 0.98 |
| Glumetza 1000 mg + Januvia 100 mg | 12580 | 1293 | 9 | 1.23 | 0.89 |
| Glucophage XR 1000 mg + Januvia 100 mg | 14793 | 1648 | 7 | 1.44 | 1.13 |
| Example 2 | 12345 | 1353 | 6.4 | 1.20 | 0.93 |

TABLE 6

Sitagliptin Parameter

| Combination drug/day | Mean AUC0-12 (ng·hr/ML) | Mean $C_{max}$ (ng/ML) | Mean $T_{max}$ hr | AUC Ratio (Test/BID) | $C_{max}$ (Test/BID) |
|---|---|---|---|---|---|
| 2 Glucophage 500 mg + 2 Januvia 50 mg (BID) | 8.43 | 938 | 2.6 | 1 | 1 |
| Fortamet 1000 mg + Januvia 100 mg | 7.9 | 910 | 3 | 0.94 | 0.97 |
| Glumetza 1000 mg + Januvia 100 mg | 8.9 | 980 | 1.9 | 1.06 | 1.04 |
| Glucophage XR 1000 mg + Januvia 100 mg | 9.05 | 895 | 2.25 | 1.07 | 0.95 |
| Example 2 | 8.3 | 940 | 2.4 | 0.98 | 1.00 |

EXAMPLE 3

A pharmaceutical composition comprising vildagliptin 50 mg and slow release metformin hydrochloride 500 mg was manufactured as described in Example 1. Table 7 shows the representative example of a pharmaceutical composition of a slow release composition having a biguanide and a DPP IV inhibitor. The pharmaceutical composition used was 500 mg metformin hydrochloride and 50 mg of Vildagliptin.

TABLE 7

| | Amount mg/tablet |
|---|---|
| First Active Ingredient | |
| Metformin HCl | 500.0 |
| Povidone K 301 USP | 36.0 |
| Sodium Lauryl Sulfate | 25.8 |
| Magnesium Stearate | 2.8 |
| Seal Coat | |
| Opadry Clear (YS 1-7006) | 23.5 |
| Semi permeable coat | |
| Cellulose Acetate (398-10) NF | 21.5 |
| Triacetin | 1.4 |
| PEG 400 | 2.8 |
| Second Active Ingredient | |
| Vildagliptin | 50.0 |
| Tween | 2.1 |
| Polyplasdone XL | 14.5 |
| Opadry Clear (YS 1-7006) | 8.5 |

EXAMPLE 4

A pharmaceutical composition comprising saxagliptin 5 mg and slow release metformin hydrochloride 500 mg was manufactured as described in Example 1. Table 8 shows the representative example of a pharmaceutical composition of a slow release composition having a biguanide and a DPP IV inhibitor. The pharmaceutical composition used was 500 mg metformin hydrochloride and 5 mg of Saxagliptin.

TABLE 8

|  | Amount mg/tablet |
|---|---|
| First Active Ingredient | |
| Metformin HCl | 500.0 |
| Povidone K 301 USP | 36.0 |
| Sodium Lauryl Sulfate | 25.8 |
| Magnesium Stearate | 2.8 |
| Seal Coat | |
| Opadry Clear (YS 1-7006) | 23.5 |
| Semi permeable coat | |
| Cellulose Acetate (398-10) NF | 21.5 |
| Triacetin | 1.4 |
| PEG 400 | 2.8 |
| Second Active Ingredient | |
| Saxagliptin | 5.0 |
| Tween | 1.4 |
| Polyplasdone XL | 11.2 |
| Opadry Clear (YS 1-7006) | 5.5 |

The formulations tested in Examples 3 and 4 were manufactured according to the process described under Example 1.

EXAMPLE 5

Method of Administration

The method for treating diabetes disclosed herein, using six controlled human clinical trials. The studies included three trials where drug formulations were administered twice daily and three where the drugs administered once daily. The studies determined the efficacy of dipeptidyl peptidase IV inhibitor, biguanide alone and a combination of a dipeptidyl peptidase IV inhibitor and a slow release biguanide; for example metformin for the treatment of non-insulin dependent diabetes mellitus (NIDDM). The trials were designed to target a segment of the type 2 diabetes population wherein the disease state has progressed to a point where maximum doses of metformin are usually required. The patients chosen were at a stage where the stimulated pancreatic insulin secretion does not keep up with the increasing demand. Since the un-stimulated (metformin) insulin secretory capacity of the beta cells is very low in this population, a reversal of insulin resistance alone would be of partial benefit. Therefore, maintaining a level of stimulated insulin secretion with a metformin while adding a dipeptidyl peptidase IV inhibitor to improve insulin sensitivity could provide a level of glycemic control unattainable by either medication alone.

A primary objective of the studies was to assess the efficacy of a dipeptidyl peptidase IV inhibitor in combination with a slow release biguanide in patients with type 2 diabetes by comparing changes in markers of glycemic and lipid homeostasis.

The effect of treatment on the pattern of post-prandial glucose tolerance (standard 2-hour meal tolerance test) was determined in a subset of patients. Brief summaries and clinical protocols and the results of these studies are presented below.

Clinical Trial I: Slow Release Metformin and Sitagliptin
1. Drugs:
Sitagliptin: Januvia 50 mg,
Immediate release Metformin Hydrochloride: Glucophage 500 mg,
Slow Release Metformin: a) Example 1, b) Glumetza XL 500 mg, c) Fortamet 500 mg and d) Glucophage XR 500 mg
2. Treatment Combination

| Treatment | Drugs: per day per patient |
|---|---|
| 1. Treatment A; | Januvia 100 mg |
| 2. Treatment B: | Glucophage 1000 mg |
| 3. Treatment C; | Januvia 100 mg + Glucophage XR 1000 mg |
| 4. Treatment D: | Januvia 100 mg + Fortamet 1000 mg |
| 5. Treatment E: | Januvia 100 mg + Glumetza 1000 mg |
| 6. Treatment: F | Example 1 Fixed dose |

3. Dosage:
The administered dosage comprised either sitagliptin (50 mg) or an immediate release metformin hydrochloride 500 mg or a combination of sitagliptin phosphate (50 mg) and slow release metformin (500 mg) selected from Treatments C, D, E and F all drug formulations administered twice a day to the patients in a long-term clinical trial.

4. Clinical Parameters:
The objectives of the invention were set by measuring following two parameters in the clinical trials:
1. Fasting Plasma Glucose: Changes in fasting plasma glucose (FPG) during sitagliptin monotherapy and during the combination comprising sitagliptin and a slow release metformin hydrochloride. The fasting plasma glucose test is a carbohydrate metabolism test which measures plasma, or blood, glucose levels after a fast. Fasting stimulates the release of the hormone glucagon, which in turn raises plasma glucose levels. In people without diabetes, the body will produce and process insulin to counteract the rise in glucose levels. In people with diabetes this does not happen, and the tested glucose levels will remain high.
2. Hemoglobin: Changes in hemoglobin A1c ($HbA_{1c}$) during 3 months of monotherapy of sitagliptin and after an additional 3 months of combination therapy (sitagliptin phosphate and slow release metformin hydrochloride). The hemoglobin A1c test shows if a person's blood sugar is close to normal or too high.
5. General Methods:
a. Change Measurement:
The trial used the methodology to compare the baseline clinical laboratory parameters with the values at the end of the study or last visit to identify any abnormal trends. The percent of patients with increases or decreases in laboratory values were calculated based on the number of patients at risk for changes outside of the reference range. Here the patients with low or high values at baseline were not considered at risk for a decrease or increase, respectively. No clinically adverse trends were noted in any laboratory parameter. However, dramatic decrease in urine glucose for all combination therapy groups was evident indicating significant improvement. Laboratory results were then reviewed for these particular patients to determine which patients actually had clinically important changes in a given laboratory parameter. Minimal changes occurred within any laboratory parameter across all treatments. A greater number of patients treated with sitagliptin and slow release metformin combination therapy than with either sitagliptin or metformin monotherapy had laboratory changes meeting clinically meaningful change criteria.

b. Adverse Events:

Among patients treated with sitagliptin and a slow release metformin combination therapy, about 10% of patients had adverse events compared with 8% and 10% of patients treated with sitagliptin and metformin monotherapy. Patients treated with combination therapy with different treatments E, D, E and F did not have statistically significant variation.

6. Laboratory Parameters

Hematology: Minimal changes occurred with any of the hematological parameters. Changes that met criteria for possible clinical importance were increases or decreases within the normal range or transient changes that subsequently resolved.

Patients meeting clinically meaningful changes in hematology parameters are classified based on the reasons.

Total Hemoglobin/Hematocrit Changes: 4%
 a. Transient decreases which returned to baseline levels: 1.0%
 b. Below normal limits throughout the trial: 1.5%
 c. Miscellaneous reasons other than trial: 3.1%

No patient experienced clinically important decreases in any hematological parameter that can be directly attributable to the administration of sitagliptin. Among the liver enzymes analysis, it was found only 2.3% had any clinically meaningful elevations in the ALT and AST. Further analysis again concluded that sitagliptin was not responsible for the variations.

Clinical Trial II: Slow Release Metformin and Vildagliptin Protocol

TITLE: A Prospective, Open, Randomized, Comparative, Four-Arm, Parallel-Group Study To Evaluate The Efficacy And Tolerability Of 1) Fixed dose combination (FDC) of Vildagliptin 50 mg and Metformin slow release 500 mg (Example 3) administered and 2) Vildagliptin 50 mg plus Glucophage XL 500 mg co-administered twice daily versus Glucophage XL 500 mg (2 tablets), Vildagliptin 50 mg, all formulations administered two times daily orally for their blood glucose lowering effect in patients with type-2 diabetes mellitus who are inadequately controlled on Metformin 1500 mg daily for 12 weeks.

SAMPLE SIZE: A total of 88 patients were enrolled, assigned about 20 in each of the four treatment arms.

INVESTIGATION DRUGS: 1) FDC containing Vildagliptin 50 mg plus slow release Metformin 500 mg administered twice daily and, 2) Vildagliptin 50 mg and Glucophage XR 500 mg co-administered twice daily INDICATION(s): Patients with type-2 diabetes mellitus who are inadequately controlled on Metformin 1500 mg daily STUDY DESIGN: A 12 week, open, randomized, controlled, multi-center, parallel run, efficacy & tolerability study designed to evaluate the efficacy of 1) Fixed dose combination (FDC) of Vildagliptin 50 mg and Metformin slow release 500 mg (Example 3) and 2) Vildagliptin 50 mg plus Glucophage XL 500 mg co-administered versus Glucophage XL 500 mg (2 tablets), Vildagliptin 50 mg. All formulations are administered two times daily orally, for their blood glucose lowering effect in patients with type-2 diabetes mellitus who are inadequately controlled on Metformin 1500 mg daily for 12 weeks PRIMARY OBJECTIVE: Was to compare the efficacy of 1) Fixed dose combination (FDC) of Vildagliptin 50 mg and Metformin slow release 500 mg (Example 3) and 2) Co-Administration of Vildagliptin 50 mg plus Glucophage XL 500 mg versus Metformin slow release 500 mg (2 tablets), Vildagliptin 50 mg, all formulations administered two times daily orally for their blood glucose lowering effect in patients with type-2 diabetes mellitus who are inadequately controlled on Metformin 1500 mg daily for 12 weeks This was carried out by:
 Monitoring the glycosylated hemoglobin (HbA1c) and fasting plasma glucose.
 Samples for HbA1c & glucose will be taken at Screening (V1), Baseline (V2), 6 Weeks (V3), and 12 Weeks (V4).

Secondary Objective: Was to compare the tolerability of 1) Fixed dose combination (FDC) of Vildagliptin 50 mg and Metformin slow release 500 mg (Example 3) administered and 2) Vildagliptin 50 mgplus Glucophage XL 500 mg co-administered twice daily versus Metformin slow release 500 mg (2 tablets), Vildagliptin 50 mg, all formulations administered two times daily orally for their blood glucose lowering effect in patients with type-2 diabetes mellitus who are inadequately controlled on Metformin 1500 mgdaily for 12 weeks. This was carried out by:
 Documenting the number and seriousness of hypoglycaemic events,
 Documenting the drop-out rate,
 Documenting haematological, liver and renal function and lipid parameters at Screening, Baseline and study conclusion (12 weeks)
 Monitoring AEs throughout the study
 Patients overall satisfaction was assessed by standard Diabetes Treatment Satisfaction Questionnaire (DTSQc)

DIAGNOSIS AND KEY SUBJECTS SELECTION CRITERIA: Subjects were male or female between the age group of 18 to 75 years, both inclusive, with at least a 1-year history of Type-2 Diabetes Mellitus not controlled by oral Metformin 1500 mg daily for at-least 12 weeks. Subjects must otherwise be in good general health.

Inclusion Criteria:

Subjects satisfied all of the following inclusion criteria to participate in the study:
 1. Was a male or female between the ages 18 to 75 years;
 2. Had at least a 1-year history of Type-2 DM;
 3. Was inadequately controlled diabetes with Metformin 1500 mgper day for at-least 12 weeks prior to screening and not receiving any other oral anti diabetic agent(s);
 4. On current physical examination, vital signs or ECG at screening that reveals no clinically significant abnormalities;
 5. Had a body mass index (BMI) between 25 to 45 kg/m2 both inclusive;
 6. Had a glycosylated haemoglobin HbA1c between 7 to 10% both inclusive;
 7. Was willing to follow the American Diabetes Association or the International Diabetes Federation diet guidelines for Type-2 Diabetes Mellitus; was able to record hypoglycaemic symptoms and other adverse events;
 8. Provided written informed consent prior to admission into the study; and
 9. If female of childbearing potential, used a reliable form of birth control and be willing to continue as such for the duration of the study.

Exclusion Criteria:

Patients excluded from the study if they meet any of the following exclusion criteria:
 1. Had a history suggestive of, or presence of significant cardiac, gastrointestinal, endocrine, neurological, liver, or kidney disease, or conditions known to interfere with the absorption, distribution, metabolism, or excretion of study drugs;
 2. Had a history of drug or alcohol dependency or psychological disease;

3. Required regular use of medication (other than study medication) that interferes with the absorption and/or metabolism of study drugs; subjects on concomitant medications that alter blood glucose levels (e.g., steroids);
4. Participated in a clinical trial or use of an investigational drug within 30 days prior to admission to this study;
5. Had an episode of severe hypoglycemia with seizure or coma within the past year;
6. Had a diagnosis of Type-1 Diabetes Mellitus;
7. Were on Insulin therapy within one year;
8. Had a history of ketoacidosis within 6 months prior to admission to this study;
9. Had a history of myocardial infarction, coronary artery bypass surgery, post-transplantation cardiomyopathy or stroke within the previous 6 months;
10. Had any acute illness within 2 weeks prior to Screening;
11. Had elevated liver enzymes (ALT, AST, alkaline phosphatase), as follows: if values for any two of the liver enzymes is >3 times the upper limit of normal;
12. Had elevated renal parameters (Blood urea nitrogen & serum creatinine), as follows: if value for any of the parameters is >3 times the upper limit of normal;
13. Subjects who had participated in any clinical trial or use of an investigational drug within 30 days prior to admission to this study;
14. Was a pregnant or lactating female patient;

STUDY DESIGN & PROCEDURES: This was a 12 week, open, randomized, controlled, multi-center, parallel run, efficacy & tolerability study designed to evaluate the efficacy of 1) Fixed dose combination (FDC) of Vildagliptin 50 mg and Metformin slow release 500 mg (Example 3) and 2) Vildagliptin 50 mg plus Glucophage XL 500 mg co-administered versus Glucophage XL 500 mg (2 tablets), Vildagliptin 50 mg, all formulations administered two times daily orally, for their blood glucose lowering effect in patients with type-2 diabetes mellitus who are inadequately controlled on Metformin 1500 mg daily for 12 weeks Patients were required to make 4 visits during the study period. After a Screening visit (V1) to determine eligibility, each subject will return at the baseline visit (V2), where they will be instructed about the dosing schedules & diet.

Subjects were required take the study medications as tablets administered orally two times in a day in the morning before breakfast and at bedtime with a glass of water.

All subjects were monitored by the Investigators and/or by the study coordinator by phone and regular clinic visits.

At every scheduled visit, subjects reported their general well being and any reported AEs. If subjects had problems or if there was a continuous deterioration of fasting plasma glucose or patient condition without known clinical reasons, the investigator reassessed the subject to determine if they could continue with the study.

If the subjects are terminated from the study, the subject was followed by the investigator to assure proper medical care was provided, and once stable, returned to the primary health care provider.

The following procedures were carried out during the study:
Screening (Visit 1, Day-10 to -2):
Study related procedures were explained and informed consent was taken.
Detailed medical history was collected.
Demographic data was collected.
An abbreviated physical examination including weight and vital signs (blood pressure, heart rate, temperature, respiration rate) was conducted.
Vital signs were obtained after the patient has been in a supine position for at least 5 minutes.
Fasting blood samples for plasma glucose, serum insulin, C-peptide & lipid profile was collected.
Blood samples were collected for haematological, liver function test, renal function, & urine analysis will be done.
Thyroid function (TSH), HIV status, 12 lead ECG was performed.
Serum pregnancy tests in women of child-bearing potential were performed.
Administrated the checklist for Inclusion / exclusion criteria.
Baseline (Visit 2, Day-2 to 1):
Physical examination was conducted.
Vital signs were evaluated.
Fasting blood samples for plasma glucose, serum insulin, C-peptide & lipid profile were collected.
Blood samples collected and haematological, liver function test, renal function, & urine analyses were done.
Baseline AEs (if any) were recorded.
Administrated the checklist for inclusion/exclusion criteria.
Drugs were dispensed and diet instructions will be given.
Patient diary was given to patient and instructions were given for filling the diary.
Week 6 (Visit 3):
Physical examination was conducted.
Vital signs were recorded.
Fasting blood samples for plasma glucose, serum insulin, C-peptide, & lipid profile were collected.
Blood samples collected and fasting plasma glucose & urine analyses were done.
All AEs & SAE's (if any) were recorded and necessary action was taken.
Patient compliance for diet & medication were recorded by interview and tablet count.
Drugs were dispensed and diet instructions were given.
Week 12 (Visit 4):
Physical examination was conducted.
Vital signs were recorded.
Fasting blood samples for plasma glucose, serum insulin, C-peptide & lipid profile were collected.
All AEs & SAE's (if any) recorded and necessary action was taken if needed.
Patient compliance for diet & medication was recorded by interview and tablet count.
Diabetes Treatment Satisfaction Questionnaire (DTSQ) will be filled by patient Over the course of the study, subjects consumed regular meals as suggested by the National Cholesterol Education Program (NCEP) ATP III (Adult Treatment Panel III) in therapeutic life style changes (TLC) nutrition component. All adverse events were recorded in the patient diary throughout the study and evaluated by the investigator upon Site Visits.
Outcome Measures
Primary Outcome Measure:
Percent change in HbA1C from baseline after 24 weeks of treatment.
Secondary Outcome Measures (after 24 weeks):
Percent change in fasting plasma glucose,
Percent change in body weight,
Responder rates for HbA1C (target<7%),
Responder rates for body weight (target BMI<25 kg/m2), Change from baseline in lipid profile.
Safety Measures:
Physical examination.
Vital Signs.
Reporting of Adverse Events (AE's) & Serious Adverse Events (SAE's)
Abnormal laboratory values of laboratory safety parameters.

Treatments
Investigational Treatment:
1. FDC containing Vildagliptin 50 mgplus slow release Metformin 500 mg (Example 3) administered twice daily
2. Vildagliptin 50 mg and Glucophage XR 500 mg co-administered twice daily.

Comparator Treatments:
3. Metformin XL 500 mg two tablets two times in a day.
4. Vildagliptin 50 mg two times in a day.

Statistics
Sample Size: As this was a pilot study, sample size is not based on any statistical calculations.

Analysis Populations Analysis populations included the per-protocol (PP) population & intention to treat (ITT) population.

Data expression: All parametric data expressed as Mean ±1 S.D. (1 Standard Deviation). Proportions are expressed as numbers & percentages. For all statistical tests, the significance level were taken as $p<0.05$ at 95% C.I.

Data Analysis: No interim analysis was planned for this study.

Normality testing was be done using Kolmogorov-Smirnov test, if data found to be normal, One-Way ANOVA was used for comparison of multiple treatments for change in HbA1C, fasting plasma glucose, body weight & lipid profile. Post-hoc multiple comparisons would be made for investigational treatment vis-a-vis the 5 comparator treatments using Tukey's test.

Responder rates & proportions were tested using Chi-square test.

orally for their blood glucose lowering effect in patients with type-2 diabetes mellitus who are inadequately controlled on Metformin 1500 mg daily for 12 weeks.

SAMPLE SIZE A total of 90 patients were enrolled, assigned about 20 in each of the four treatment arms.

INVESTIGATION DRUGS: 1) FDC containing Saxagliptin 5 mg plus slow release Metformin 500 mg administered twice daily and, 2) Saxagliptin 5 mg and Glucophage XR 500 mg co-administered twice daily INDICATION(s): Patients with type-2 diabetes mellitus who are inadequately controlled on Metformin 1500 mg daily STUDY DESIGN: This was a 12 week, open, randomized, controlled, multi-center, parallel run, efficacy & tolerability study designed to evaluate the efficacy of 1) Fixed dose combination (FDC) of Saxagliptin 5 mg and Metformin slow release 500 mg (Example 4) and 2) Saxagliptin 5 mg plus Glucophage XL 500 mg co-administered versus Glucophage XL 500 mg (2 tablets), Saxagliptin 5 mg, all formulations administered two times daily orally, for their blood glucose lowering effect in patients with type-2 diabetes mellitus who are inadequately controlled on Metformin 1500 mg daily for 12 weeks PRIMARY OBJECTIVE: Was to compare the efficacy of 1) Fixed dose combination (FDC) of Saxagliptin 5 mg and Metformin slow release 500 mg (Example 4) and 2) Co-Administration of Saxagliptin 5 mg plus Glucophage XL 500 mg versus Metformin slow release 500 mg (2 tablets), Saxagliptin 5 mg, all formulations administered two times daily orally for their blood glucose lowering effect in patients with type-2 diabetes mellitus who are inadequately controlled on Metformin 1500 mg daily for 12 weeks This was carried out by:
Monitoring the glycosylated hemoglobin (HbA1c) and fasting plasma glucose.
Samples for HbA1c & glucose will be taken at Screening (V1), Baseline (V2), 6 Weeks (V3), and 12 Weeks (V4).
Secondary Objective: Was to compare the tolerability of 1) Fixed dose combination (FDC) of Saxagliptin 5 mg and Metformin slow release 500 mg (Example 4) administered two

| Vildagliptin Study, Patient Characteristics | | | | |
|---|---|---|---|---|
| Characteristic | Vildagliptin 50 mg | Glucophage 500 mg | Vildagliptin 50 mg + Glucophage XR 500 mg | Vildagliptin 50 mg + Metformin 500 mg (FDC) |
| N | 22 | 21 | 22 | 23 |
| Mean age +/− SD (y) | 44 ± 2.2 | 45 ± 2.8 | 43 ± 3.2 | 42 ± 4.1 |
| Sex (M:F) | 11; 11 | 10; 11 | 10; 12 | 13; 10 |
| BMI | 34 ± 3.3 | 33 ± 4.3 | 32 ± 3.8 | 34 ± 2.5 |
| Mean HbA1c (%) | 8.4 | 8.6 | 8.5 | 8.65 |
| Mean FPG (mg/dl) | 243 | 244 | 246 | 245 |
| Disease Duration (Years) | 5 | 4 | 6 | 7 |

Clinical Trials III: Slow Release Metformin and Saxagliptin
Protocol
TITLE: A Prospective, Open, Randomized, Comparative, Four-Arm, Parallel-Group Study To Evaluate The Efficacy And Tolerability Of 1) Fixed dose combination (FDC) of Saxagliptin 5 mg and Metformin slow release 500 mg (Example 4) administered two times daily orally and 2) Saxagliptin 5 mg plus Glucophage XL 500 mg co-administered twice daily versus Glucophage XL 500 mg (2 tablets), Saxagliptin 5 mg all formulations administered two times daily times daily orally and 2) Saxagliptin 5 mg plus Glucophage XL 500 mg co-administered twice daily versus Metformin slow release 500 mg (2 tablets), Saxagliptin 5 mg, all formulations administered two times daily orally for their blood glucose lowering effect in patients with type-2 diabetes mellitus who are inadequately controlled on Metformin 1500 mgdaily for 12 weeks. This was carried out by:

Documenting the number and seriousness of hypoglycaemic events,
Documenting the drop-out rate, Documenting haematological, liver and renal function and lipid parameters at Screening, Baseline and study conclusion (12 weeks)

Monitoring AEs throughout the study

Patients overall satisfaction was assessed by standard Diabetes Treatment Satisfaction Questionnaire (DTSQc)

Treatments

Investigational Treatment:
1. FDC containing Saxagliptin 5 mg plus slow release Metformin 500 mg (Example 4) administered twice daily
2. Saxagliptin 5 mg and Glucophage XR 500 mg co-administered twice daily.

Comparator Treatments:
3. Metformin XL 500 mg two tablets two times in a day.
4. Saxagliptin 5 mg two times in a day.

Study design and procedures, statistics, outcome measure, inclusion and exclusion criteria were similar to Clinical Trial II.

Metformin slow release 500 mg (Example 1)-Two Tablets and 2) Glucophage XL 500 mg (2 tablets), 3) Sitagliptin 50 mg (2 tablets), all drugs administered once daily orally, for their blood glucose lowering effect in patients with type-2 diabetes mellitus who are inadequately controlled on Metformin 1500 mg daily for 4 weeks.

This was carried out by:
Monitoring the glycosylated hemoglobin (HbA1c) and fasting plasma glucose.
Samples for HbA1c & glucose will be taken at Screening (V1), Baseline (V2), 2 Weeks (V3), and 4 Weeks (V4).

Secondary Objective: Was to compare the tolerability of 1) Fixed dose combination (FDC) of Sitagliptin 50 mg and Metformin slow release 500 mg (Example 1)-Two Tablets and 2) Glucophage XL 500 mg (2 tablets), 3) Sitagliptin 50 mg (2 tablets), all drugs administered once daily orally, for their blood glucose lowering effect in patients with type-2 diabetes mellitus who are inadequately controlled on Metformin 1500 mg daily for 4 weeks. This was carried out by:

| Saxagliptin Study, Patient Characteristics; | | | | |
|---|---|---|---|---|
| Characteristic | Saxagliptin 5 mg | Glucophage XR 500 mg | Saxagliptin 5 mg Glucophage XR 500 mg | Saxagliptin 5 mg Glucophage XR 500 mg (FDC) |
| N | 23 | 24 | 22 | 21 |
| Mean age +/− SD (y) | 45 ± 4.2 | 43 ± 3.8 | 44 ± 2.8 | 44 ± 4.4 |
| Sex (M:F) | 12; 11 | 13; 11 | 11; 11 | 11; 10 |
| BMI | 32 ± 3.3 | 34 ± 2.3 | 34 ± 4.3 | 34 ± 4.3 |
| Mean HbA1c (%) | 9.4 | 9.4 | 9.6 | 9.5 |
| Mean FPG (mg/dl) | 235 | 235 | 243 | 245 |
| Disease Duration (Years) | 5 | 6 | 4 | 5 |

Clinical Trial IV: Slow Release Metformin and Sitagliptin Protocol

TITLE: A Prospective, Open, Randomized, Comparative, Three-Arm, Parallel-Group Study To Evaluate The Efficacy And Tolerability Of 1) Fixed dose combination (FDC) of Sitagliptin 50 mg and Metformin slow release 500 mg (Example 1)-Two Tablets and 2) Glucophage XL 500 mg (2 tablets), 3) Sitagliptin 50 mg (2 tablets), all drugs administered once daily orally for their blood glucose lowering effect in patients with type-2 diabetes mellitus who are inadequately controlled on Metformin 1500 mg daily for 4 weeks.

SAMPLE SIZE A total of 66 patients were enrolled, assigned about 20 in each of the three treatment arms.

INVESTIGATION DRUGS: 1) Fixed dose combination (FDC) of Sitagliptin 50 mg and Metformin slow release 500 mg (Example 1)-Two Tablets and 2) Glucophage XL 500 mg (2 tablets), 3) Sitagliptin 50 mg (2 tablets), all drugs administered once daily orally INDICATION(s): Patients with type-2 diabetes mellitus who are inadequately controlled on Metformin 1500 mg daily STUDY DESIGN: This was a 12 week, open, randomized, controlled, multi-center, parallel run, efficacy & tolerability study designed to evaluate the efficacy of 1) Fixed dose combination (FDC) of Sitagliptin 50 mg and Metformin slow release 500 mg (Example 1)-Two Tablets and 2) Glucophage XL 500 mg (2 tablets), 3) Sitagliptin 50 mg (2 tablets), all drugs administered once daily orally, for their blood glucose lowering effect in patients with type-2 diabetes mellitus who are inadequately controlled on Metformin 1500 mg daily for 4 weeks.

PRIMARY OBJECTIVE: Was to compare the efficacy of 1) Fixed dose combination (FDC) of Sitagliptin 50 mg and Documenting the number and seriousness of hypoglycaemic events, Documenting the drop-out rate, Documenting haematological, liver and renal function and lipid parameters at Screening, Baseline and study conclusion (4 weeks)

Monitoring AEs throughout the study

Patients overall satisfaction was assessed by standard Diabetes Treatment Satisfaction Questionnaire (DTSQc)

Study design and procedures, statistics, outcome measure, inclusion and exclusion criteria were similar to Clinical Trial II except suitable modifications adjust the study design to suit a 4 week study.

The patient characteristics are listed below;

| Clinical Trial IV (Sitagliptin) Patient Characteristics | | | |
|---|---|---|---|
| Characteristic/ Treatment | Sitagliptin 50 mg X2 | Glucophage XR 500 mg X 2 | FDC (Sitagliptin 50 mg + Metfpormin XL 500 mg) X 2 |
| N | 23 | 21 | 22 |
| Mean age +/− SD (y) | 49.1 ± 2.2 | 48.22 ± 1.9 | 47.8 ± 2.4 |
| Sex (M:F) | 11; 12 | 11; 10 | 10; 12 |
| BMI | 35 ± 1.1 | 34 ± 3.3 | 34 ± 3.5 |
| Mean HbA1c (%) | 9 | 9.1 | 9.2 |
| Mean FPG (mg/dl) | 253.5 | 245 | 240.5 |
| Disease Duration (Years) | 7 | 6.5 | 7.2 |

Clinical Trial V: Slow Release Metformin and Vildagliptin Protocol

TITLE: A Prospective, Open, Randomized, Comparative, Three-Arm, Parallel-Group Study To Evaluate The Efficacy And Tolerability Of 1) Fixed dose combination (FDC) of Vildagliptin 50 mg and Metformin slow release 500 mg (Example 3)-Two Tablets and 2) Glucophage XL 500 mg (2 tablets), 3) Vildagliptin 50 mg (2 tablets), all drugs administered once daily orally for their blood glucose lowering effect in patients with type-2 diabetes mellitus who are inadequately controlled on Metformin 1500 mg daily for 4 weeks.

SAMPLE SIZE A total of 69 patients were enrolled, assigned about 20 in each of the three treatment arms.

INVESTIGATION DRUGS: 1) Fixed dose combination (FDC) of Vildagliptin 50 mg and Metformin slow release 500 mg (Example 3)-Two Tablets and 2) Glucophage XL 500 mg (2 tablets), 3) Vildagliptin 50 mg (2 tablets), all drugs administered once daily orally INDICATION(s): Patients with type-2 diabetes mellitus who are inadequately controlled on Metformin 1500 mg daily STUDY DESIGN: This was a 12 week, open, randomized, controlled, multi-center, parallel run, efficacy & tolerability study designed to evaluate the efficacy of 1) Fixed dose combination (FDC) of Vildagliptin 50 mg and Metformin slow release 500 mg (Example 3)-Two Tablets and 2) Glucophage XL 500 mg (2 tablets), 3) Vildagliptin 50 mg (2 tablets), all drugs administered once daily orally, for their blood glucose lowering effect in patients with type-2 diabetes mellitus who are inadequately controlled on Metformin 1500 mg daily for 4 weeks.

PRIMARY OBJECTIVE: Was to compare the efficacy of 1) Fixed dose combination (FDC) of Vildagliptin 50 mg and Metformin slow release 500 mg (Example 3)-Two Tablets and 2) Glucophage XL 500 mg (2 tablets), 3) Vildagliptin 50 mg (2 tablets), all drugs administered once daily orally, for their blood glucose lowering effect in patients with type-2 diabetes mellitus who are inadequately controlled on Metformin 1500 mg daily for 4 weeks.

This was carried out by:
Monitoring the glycosylated hemoglobin (HbA1c) and fasting plasma glucose.
Samples for HbA1c & glucose will be taken at Screening (V1), Baseline (V2), 2 Weeks (V3), and 4 Weeks (V4).

Secondary Objective: Was to compare the tolerability of 1) Fixed dose combination (FDC) of Vildagliptin 50 mg and Metformin slow release 500 mg (Example 3)-Two Tablets and 2) Glucophage XL 500 mg (2 tablets), 3) Vildagliptin 50 mg (2 tablets), all drugs administered once daily orally, for their blood glucose lowering effect in patients with type-2 diabetes mellitus who are inadequately controlled on Metformin 1500 mg daily for 4 weeks. This was carried out by:
Documenting the number and seriousness of hypoglycaemic events,
Documenting the drop-out rate,
Documenting haematological, liver and renal function and lipid parameters at Screening, Baseline and study conclusion (4 weeks)
Monitoring AEs throughout the study
Patients overall satisfaction was assessed by standard Diabetes Treatment Satisfaction Questionnaire (DTSQc)

Study design and procedures, statistics, outcome measure, inclusion and exclusion criteria were similar to Clinical Trial II except suitable modifications adjust the study design to suit a 4 week study.

The patient characteristics are listed below;

| Clinical Trial IV (Vildagliptin) Patient Characteristics | | | |
|---|---|---|---|
| Characteristic/ Treatment | Vildagliptin 50 mg X 2 | Glucophage XR 500 mg X 2 | FDC (Vildagliptin 50 mg + Metfpormin XL 500 mg) X 2 |
| N | 23 | 21 | 25 |
| Mean age +/− SD (y) | 48 ± 2.6 | 49.1 ± 2.2 | 44.3 ± 3.2 |
| Sex (M:F) | 11; 11 | 10; 11 | 13; 10 |
| BMI | 34 ± 3.3 | 33 ± 4.3 | 34 ± 2.5 |
| Mean HbA1c (%) | 8.8 | 9 | 9.3 |
| Mean FPG (mg/dl) | 253 | 245 | 251.1 |
| Disease Duration (Years) | 6.6 | 7 | 7.5 |

Clinical Trial VI: Slow Release Metformin and Saxagliptin Protocol

TITLE: A Prospective, Open, Randomized, Comparative, Three-Arm, Parallel-Group Study To Evaluate The Efficacy And Tolerability Of 1) Fixed dose combination (FDC) of Saxagliptin 5 mg and Metformin slow release 500 mg (Example 4)-Two Tablets and 2) Glucophage XL 500 mg (2 tablets), 3) Saxagliptin 5 mg (2 tablets), all drugs administered once daily orally for their blood glucose lowering effect in patients with type-2 diabetes mellitus who are inadequately controlled on Metformin 1500 mg daily for 4 weeks.

SAMPLE SIZE A total of 71 patients were enrolled, assigned about 20 in each of the three treatment arms.

INVESTIGATION DRUGS: 1) Fixed dose combination (FDC) of Saxagliptin 5 mg and Metformin slow release 500 mg (Example 4)-Two Tablets and 2) Glucophage XL 500 mg (2 tablets), 3) Saxagliptin 5 mg (2 tablets), all drugs administered once daily orally INDICATION(s): Patients with type-2 diabetes mellitus who are inadequately controlled on Metformin 1500 mg daily STUDY DESIGN: This was a 12 week, open, randomized, controlled, multi-center, parallel run, efficacy & tolerability study designed to evaluate the efficacy of 1) Fixed dose combination (FDC) of Saxagliptin 5 mg and Metformin slow release 500 mg (Example 4)-Two Tablets and 2) Glucophage XL 500 mg (2 tablets), 3) Saxagliptin 5 mg (2 tablets), all drugs administered once daily orally, for their blood glucose lowering effect in patients with type-2 diabetes mellitus who are inadequately controlled on Metformin 1500 mg daily for 4 weeks.

PRIMARY OBJECTIVE: Was to compare the efficacy of 1) Fixed dose combination (FDC) of Saxagliptin 5 mg and Metformin slow release 500 mg (Example 4)-Two Tablets and 2) Glucophage XL 500 mg (2 tablets), 3) Saxagliptin 5 mg (2 tablets), all drugs administered once daily orally, for their blood glucose lowering effect in patients with type-2 diabetes mellitus who are inadequately controlled on Metformin 1500 mg daily for 4 weeks.

This was carried out by:
Monitoring the glycosylated hemoglobin (HbA1c) and fasting plasma glucose.
Samples for HbA1c & glucose will be taken at Screening (V1), Baseline (V2), 2 Weeks (V3), and 4 Weeks (V4).

Secondary Objective: Was to compare the tolerability of 1) Fixed dose combination (FDC) of Saxagliptin 5 mg and Metformin slow release 500 mg (Example 4)-Two Tablets and 2) Glucophage XL 500 mg (2 tablets), 3) Saxagliptin 5 mg (2 tablets), all drugs administered once daily orally, for their blood glucose lowering effect in patients with type-2 diabetes mellitus who are inadequately controlled on Metformin 1500 mg daily for 4 weeks. This was carried out by:

Documenting the number and seriousness of hypoglycaemic events,

Documenting the drop-out rate,

Documenting haematological, liver and renal function and lipid parameters at Screening, Baseline and study conclusion (4 weeks)

Monitoring AEs throughout the study

Patients overall satisfaction was assessed by standard Diabetes Treatment Satisfaction Questionnaire (DTSQc)

Study design and procedures, statistics, outcome measure, inclusion and exclusion criteria were similar to Clinical Trial II except suitable modifications adjust the study design to suit a 4 week study.

The patient characteristics are listed below;

| Clinical Trial VI (Saxagliptin) Patient Characterstics | | | |
|---|---|---|---|
| Characteristic/ Treatment | Saxagliptin 5 mg X2 | Glucophage XR 500 mg X 2 | FDC (Saxagliptin 5 mg + Metformin XL 500 mg) X 2 |
| N | 23 | 24 | 21 |
| Mean age +/− SD (y) | 45 ± 4.2 | 43 ± 3.8 | 44 ± 4.4 |
| Sex (M:F) | 12; 11 | 13; 11 | 11; 10 |
| BMI | 32 ± 3.3 | 34 ± 2.3 | 34 ± 4.3 |
| Mean HbA1c (%) | 9.1 | 9.1 | 9.3 |
| Mean FPG (mg/dl) | 248.5 | 245 | 241.5 |
| Disease Duration (Years) | 6 | 5.3 | 5.5 |

7. Results:

The objectives of the inventions are met by the following results from the clinical trials:

FIG. 1: Illustrates a change in fasting plasma glucose (FPG) (+/−−) SEM) during sitagliptin, metformin hydrochloride monotherapy and Treatment F comprising sitagliptin phosphate and slow release metformin hydrochloride fixed dose combination.

Figure 2:
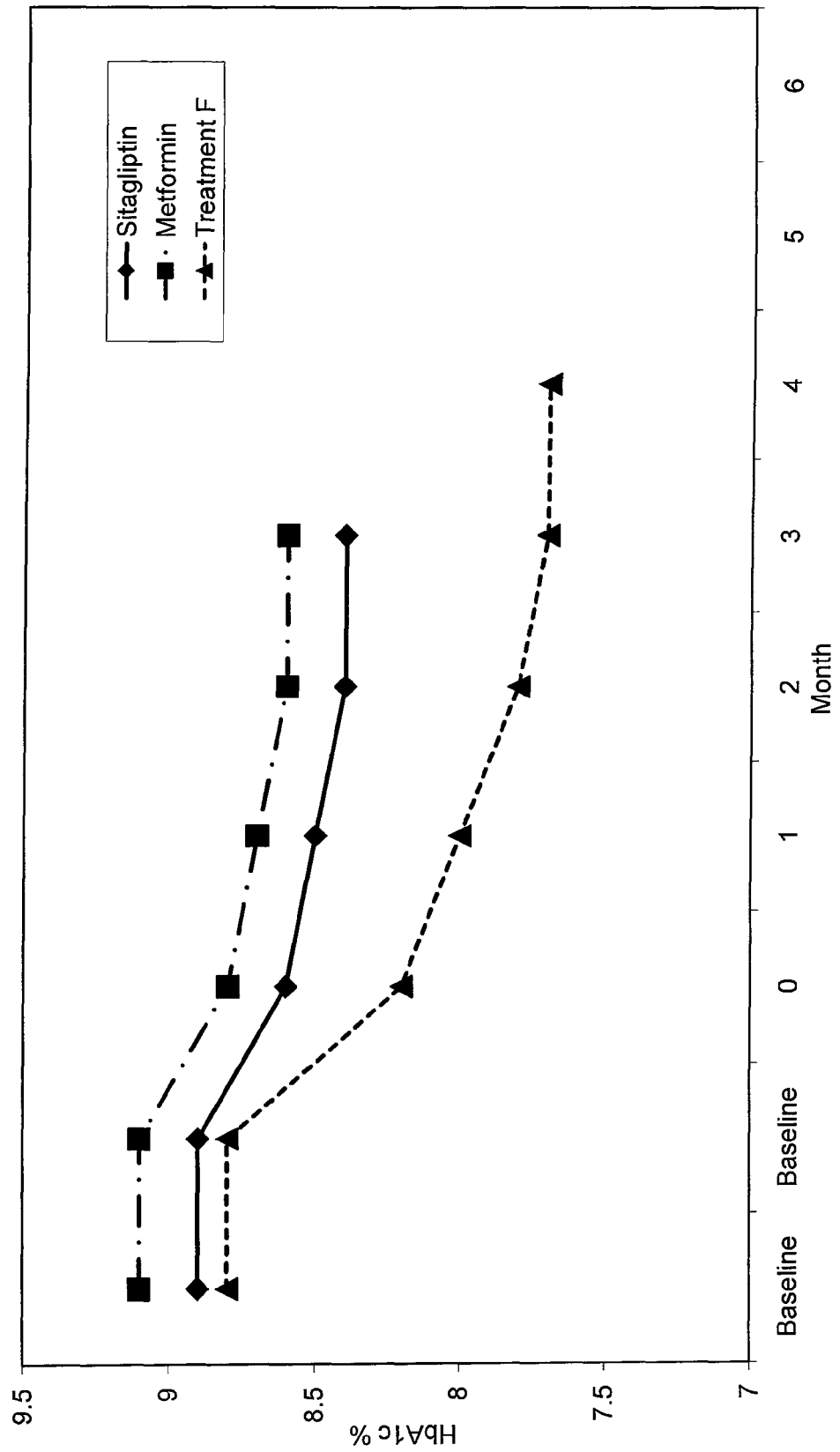
FIG. 2: Illustrates a change in hemoglobin A1c (HbA$_{1c}$) (+/−.SEM) during 3 months of sitagliptin and metformin hydrochloride monotherapy, and Treatment F comprising sitagliptin phosphate and slow release metformin hydrochloride fixed dose combination.

FIG. 2: Illustrates a change in hemoglobin A1c (HbA$_{1c}$) (+/−.SEM) during 3 months of sitagliptin and metformin hydrochloride monotherapy, and Treatment F comprising sitagliptin phosphate and slow release metformin hydrochloride fixed dose combination.

Figure 3:
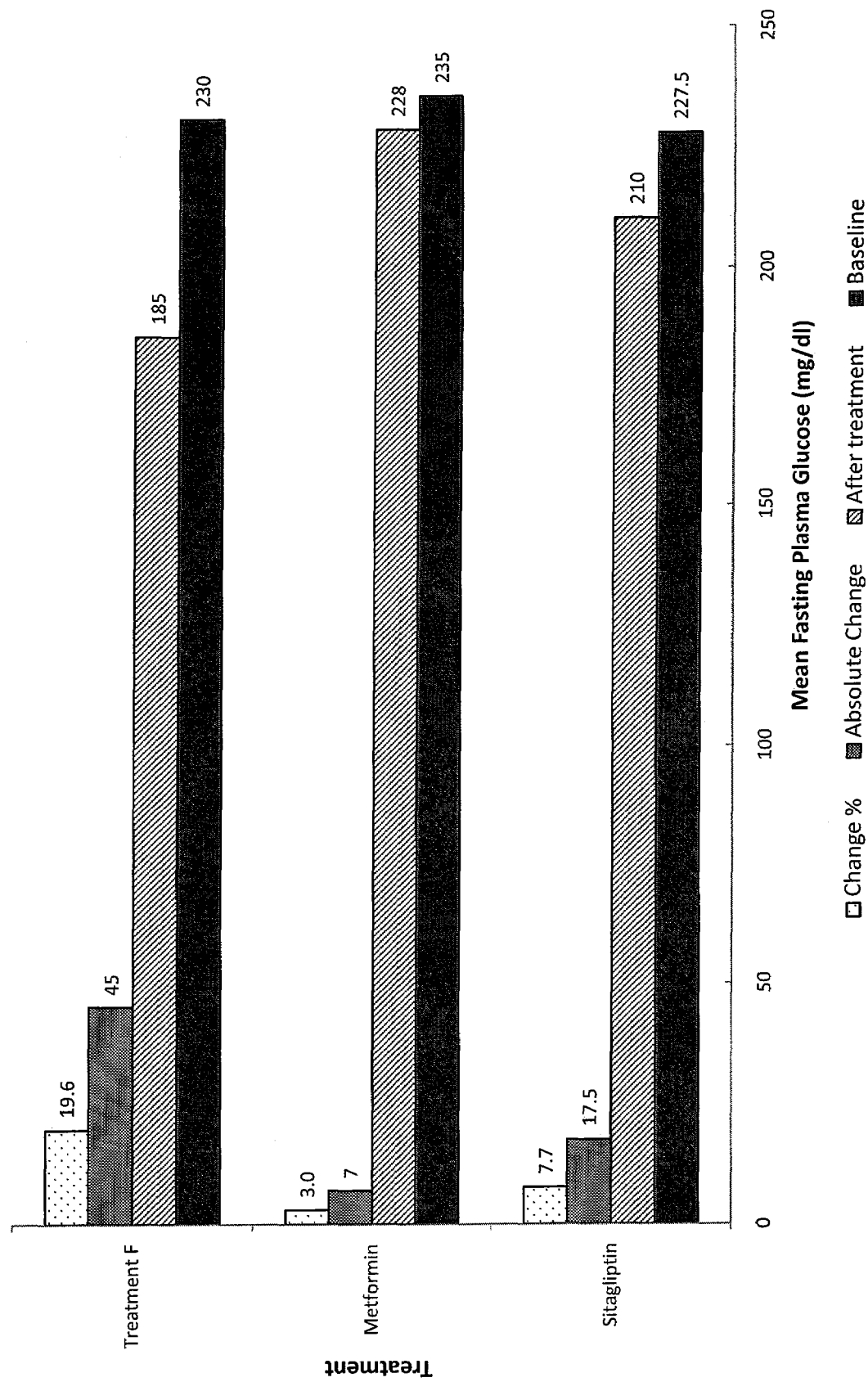
FIG. 3: Illustrates a change in mean FPG for sitagliptin, metformin monotherapy and combination therapy using Treatment F comprising sitagliptin phosphate and slow release metformin hydrochloride fixed dose combination.

FIG. 3: Illustrates a change in mean FPG for sitagliptin, metformin monotherapy and combination therapy using Treatment F comprising sitagliptin phosphate and slow release metformin hydrochloride fixed dose combination.

Figure 4:
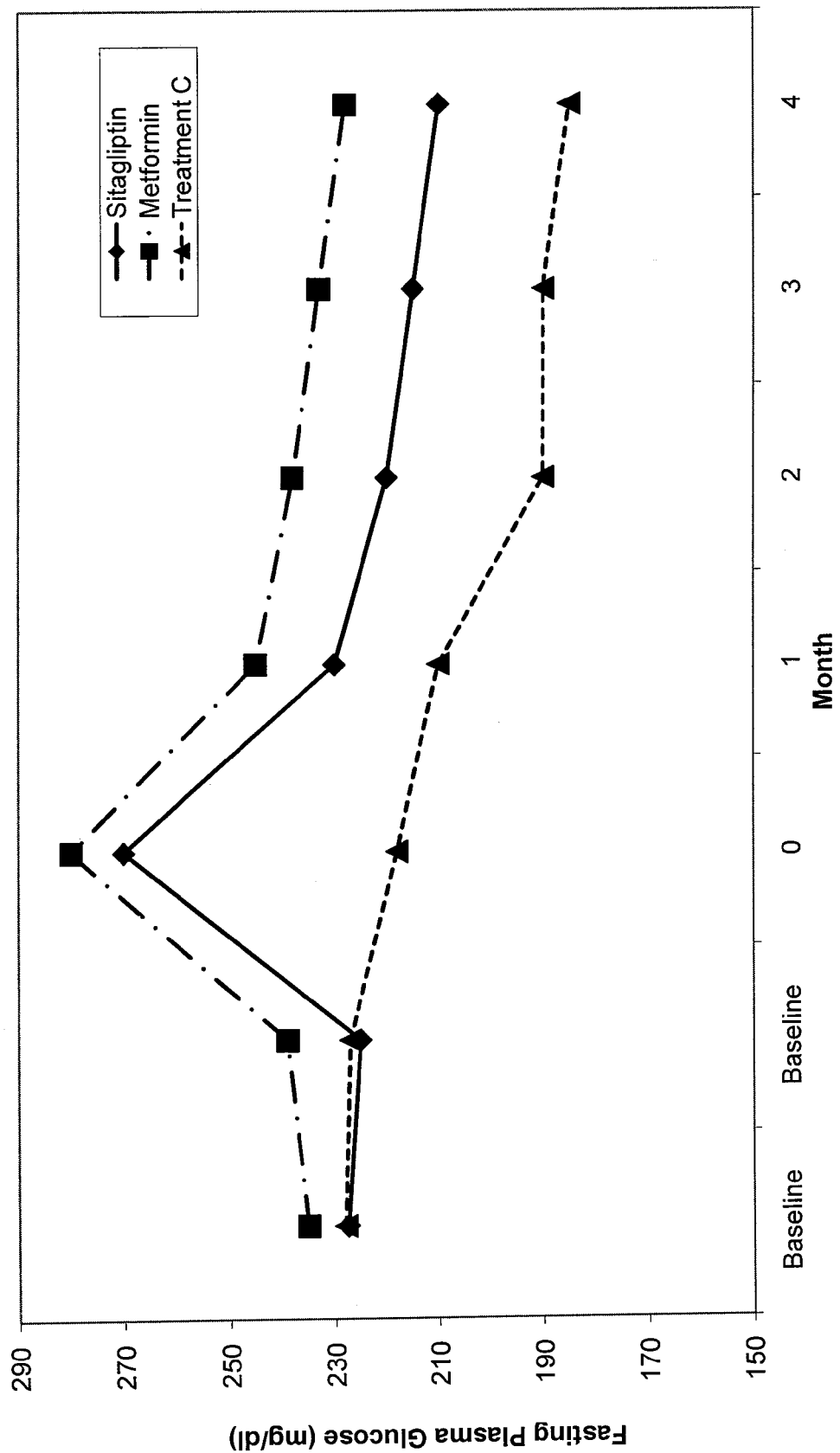
FIG. 4: Illustrates a change in fasting plasma glucose (FPG) (+/−) SEM during sitagliptin, metformin hydrochloride monotherapy and Treatment C comprising the co-administration of sitagliptin phosphate and Glucophage XR.

FIG. 4: Illustrates a change in fasting plasma glucose (FPG) (+/−−) SEM) during sitagliptin, metformin hydrochloride monotherapy and Treatment C comprising the co-administration of sitagliptin phosphate and Glucophage XR.

Figure 5:
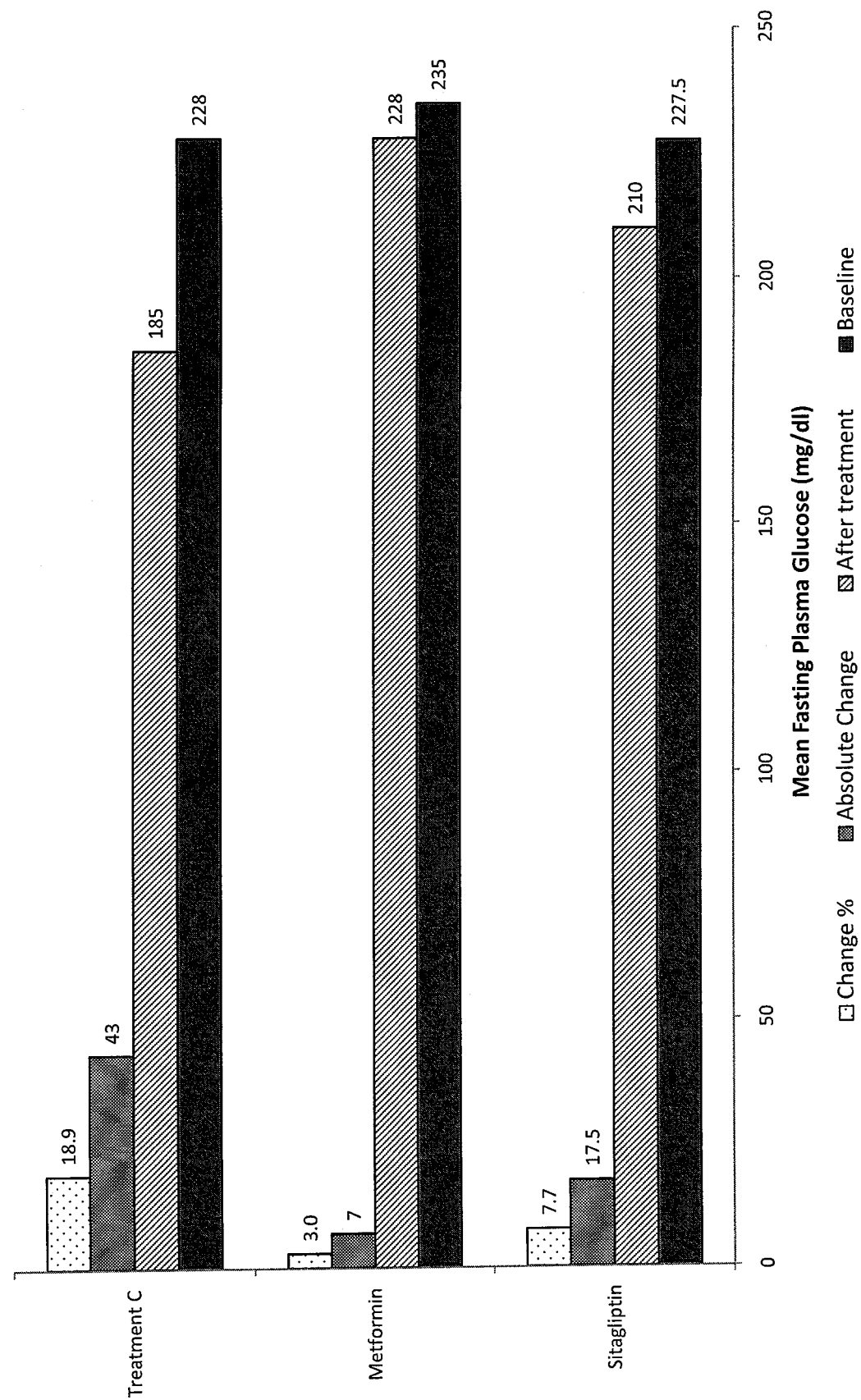
FIG. 5: Illustrates a change in mean FPG for sitagliptin, metformin monotherapy and combination therapy using Treatment C comprising the co-administration of sitagliptin phosphate and Glucophage XR.

FIG. 5: Illustrates a change in mean FPG for sitagliptin, metformin monotherapy and combination therapy using Treatment C comprising the co-administration of sitagliptin phosphate and Glucophage XR.

Figure 6:
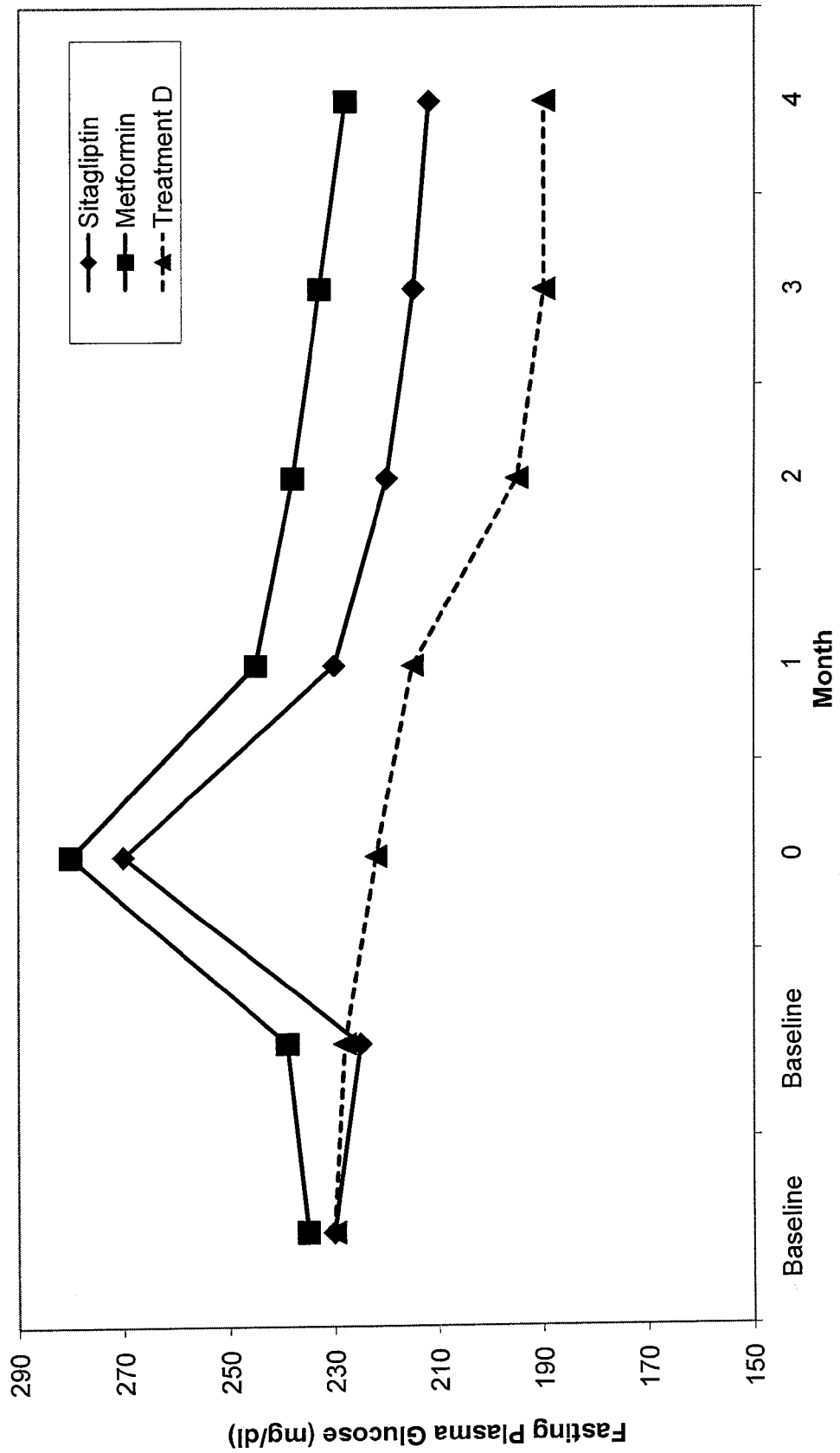
FIG. 6: Illustrates a change in fasting plasma glucose (FPG) (+/−) SEM during sitagliptin, metformin hydrochloride monotherapy and Treatment D comprising the co-administration of sitagliptin phosphate and Fortamet.

FIG. 6: Illustrates a change in fasting plasma glucose (FPG) (+/−−) SEM) during sitagliptin, metformin hydrochloride monotherapy and Treatment D comprising the co-administration of sitagliptin phosphate and Fortamet.

Figure 7:
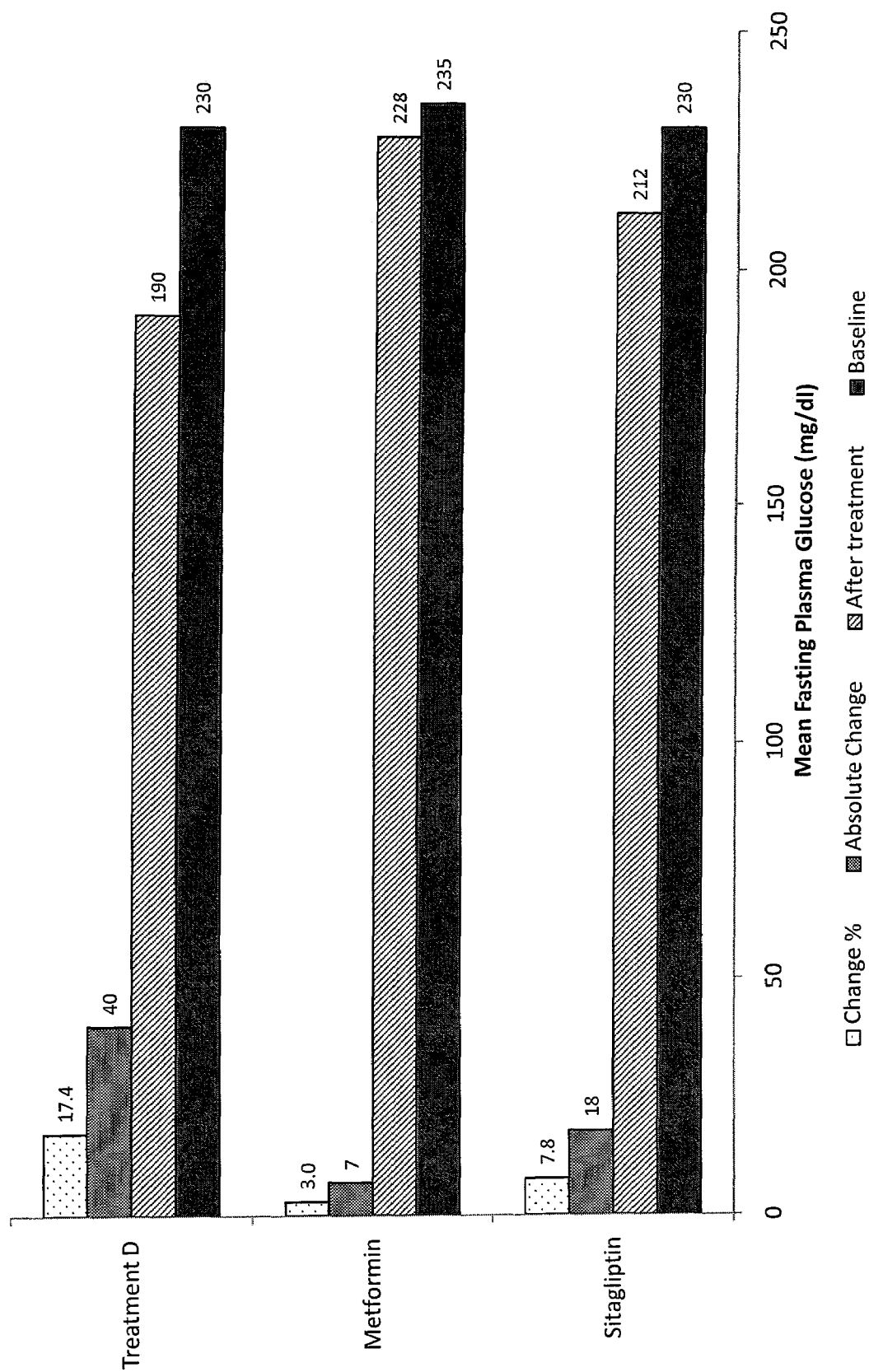
FIG. 7: Illustrates a change in mean FPG for sitagliptin, metformin monotherapy and combination therapy using Treatment D comprising the co-administration of sitagliptin phosphate and Fortamet.

FIG. 7: Illustrates a change in mean FPG for sitagliptin, metformin monotherapy and combination therapy using Treatment D comprising the co-administration of sitagliptin phosphate and Fortamet.

Figure 8:
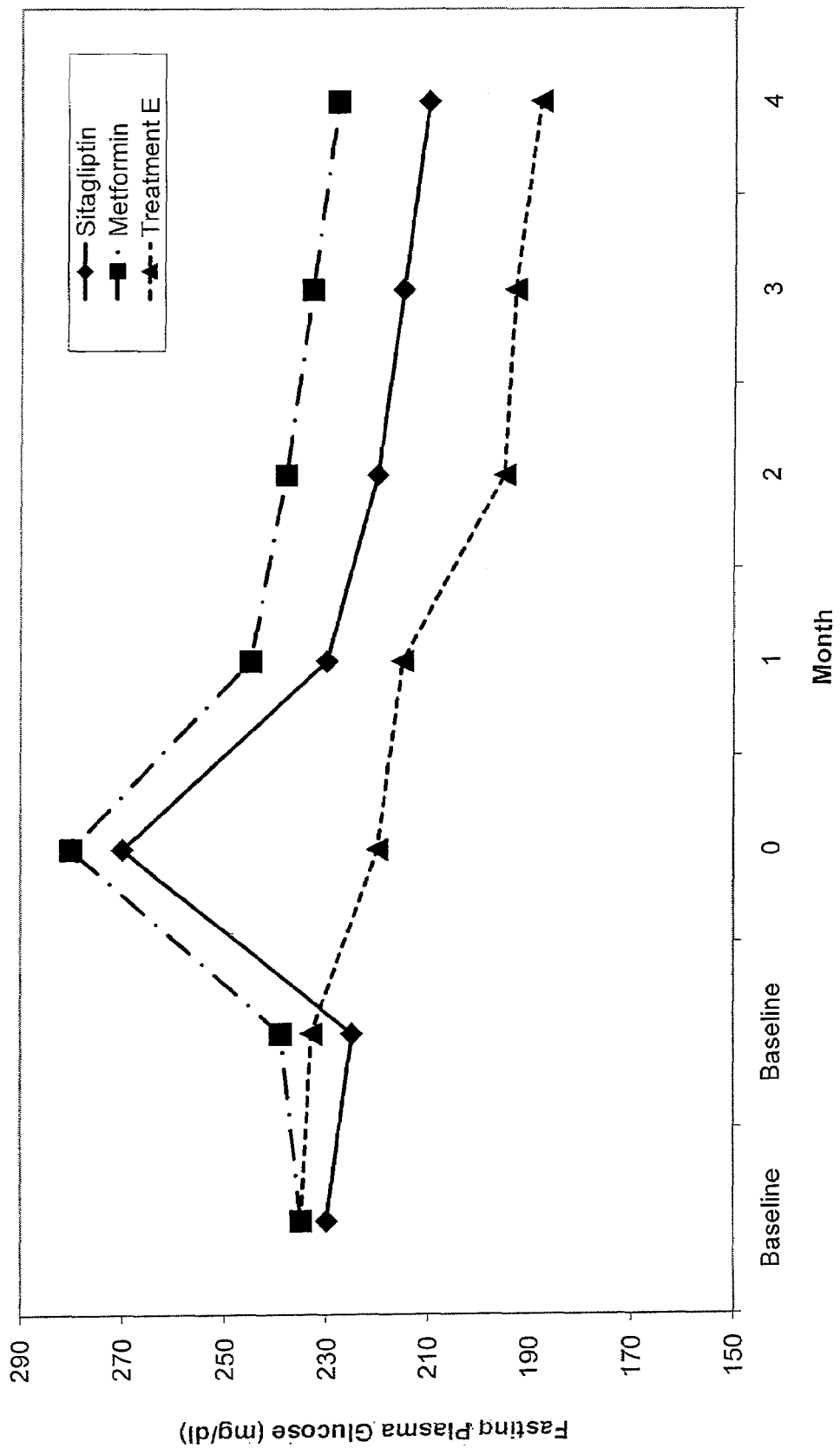
FIG. 8: Illustrates a change in fasting plasma glucose (FPG) (+/−) SEM during sitagliptin, metformin hydrochloride monotherapy and Treatment E comprising the co-administration of sitagliptin phosphate and Glumetza.

FIG. 8: Illustrates a change in fasting plasma glucose (FPG) (+/−−) SEM) during sitagliptin, metformin hydrochloride monotherapy and Treatment E comprising the co-administration of sitagliptin phosphate and Glumetza.

Figure 9:
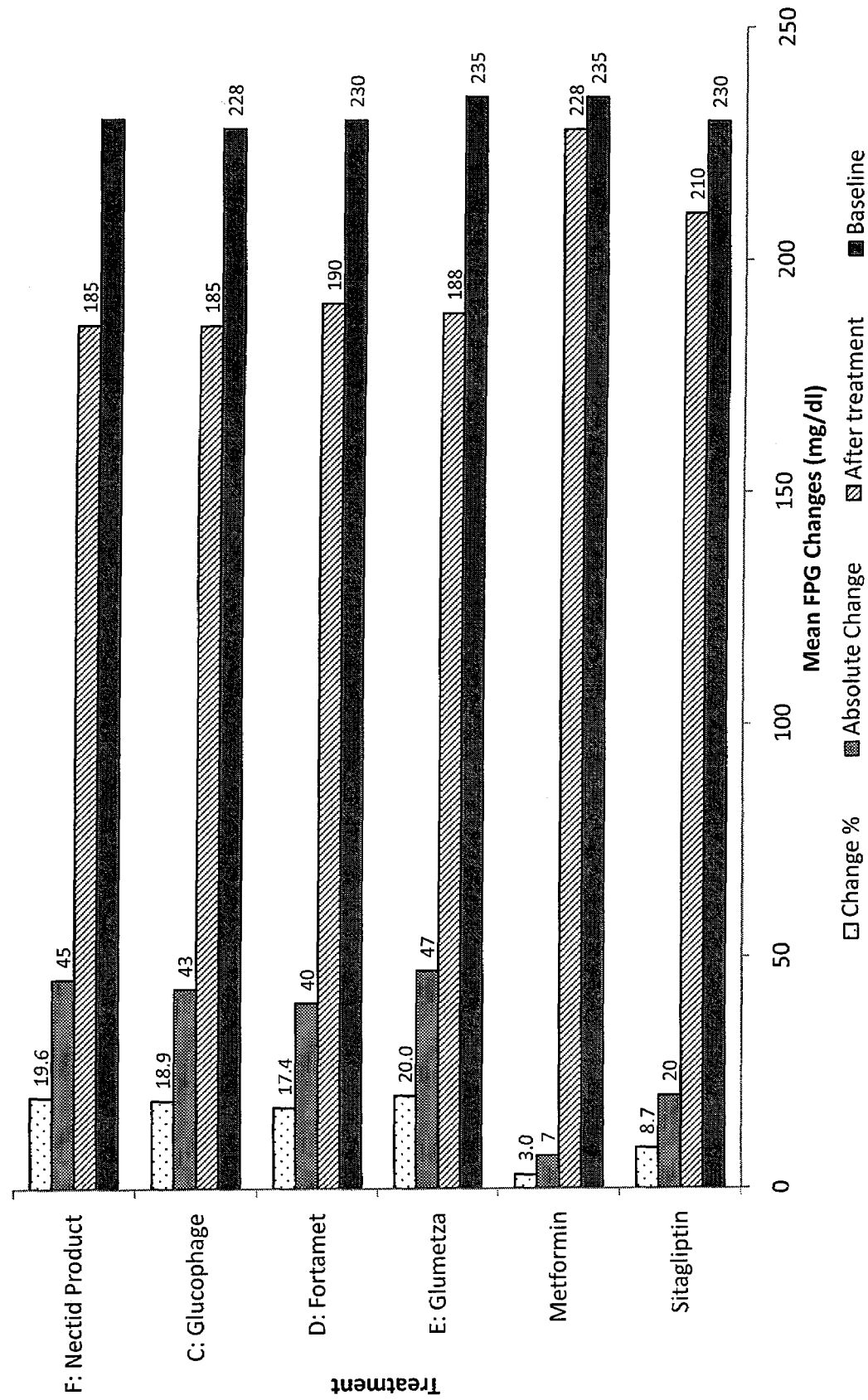
FIG. 9: Illustrates a change in mean FPG for sitagliptin, metformin monotherapy and combination therapy using Treatment E comprising the co-administration of sitagliptin phosphate and Glumetza.

FIG. 9: Illustrates a change in mean FPG for sitagliptin, metformin monotherapy and combination therapy using Treatment E comprising the co-administration of sitagliptin phosphate and Glumetza.

Figure 10:
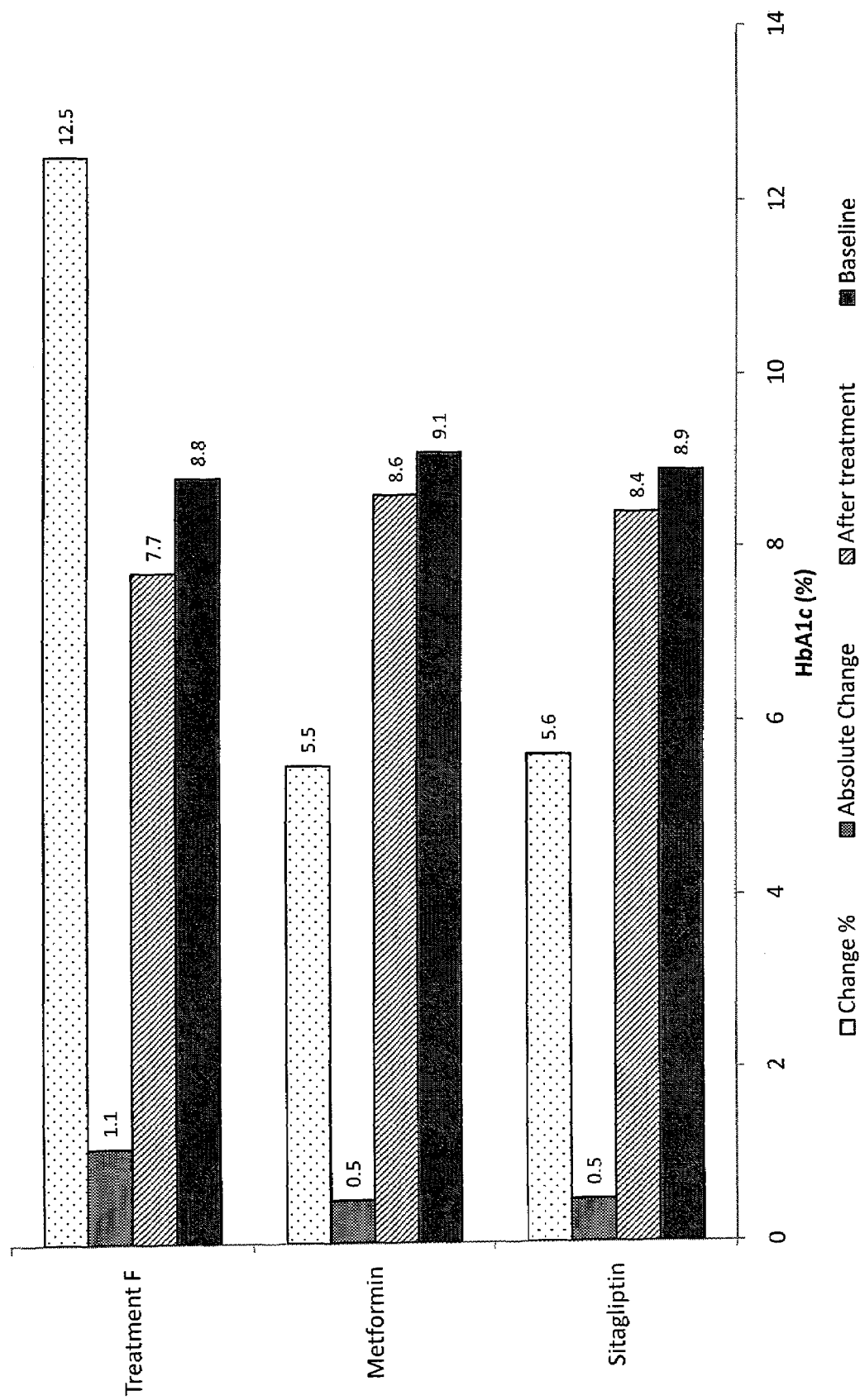
FIG. 10: Illustrates a change in mean HbA1c for sitagliptin, metformin monotherapy combination therapy using Treatment F comprising sitagliptin phosphate and slow release metformin hydrochloride fixed dose combination.

FIG. 10: Illustrates a change in mean HbA1c for sitagliptin, metformin monotherapy combination therapy using Treatment F comprising sitagliptin phosphate and slow release metformin hydrochloride fixed dose combination.

Figure 11:
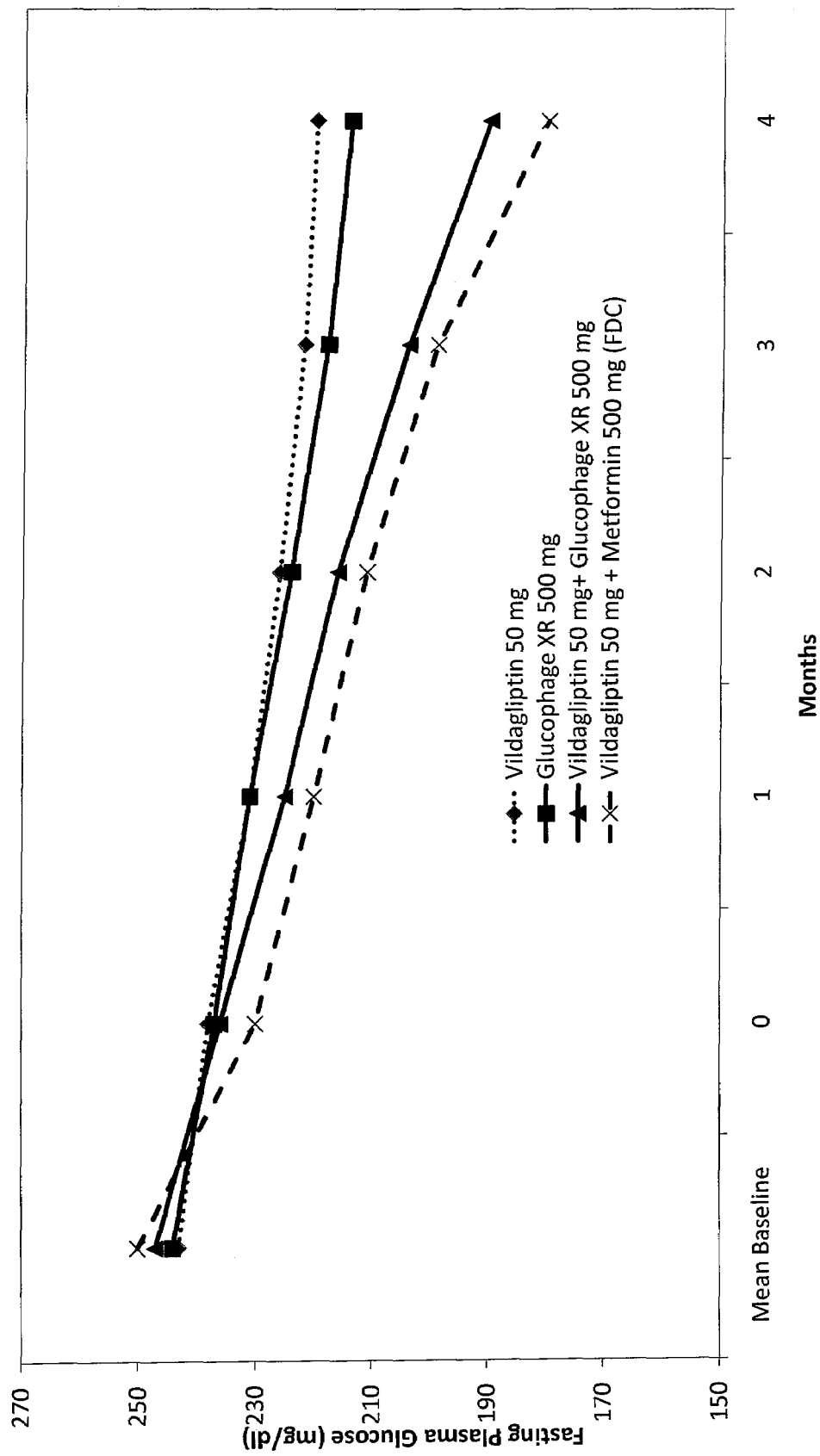
FIG. 11: Illustrates changes in fasting plasma glucose (FPG) (+/−) SEM during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

FIG. 11: Illustrates changes in fasting plasma glucose (FPG) (+/−−) SEM) during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

Figure 12:
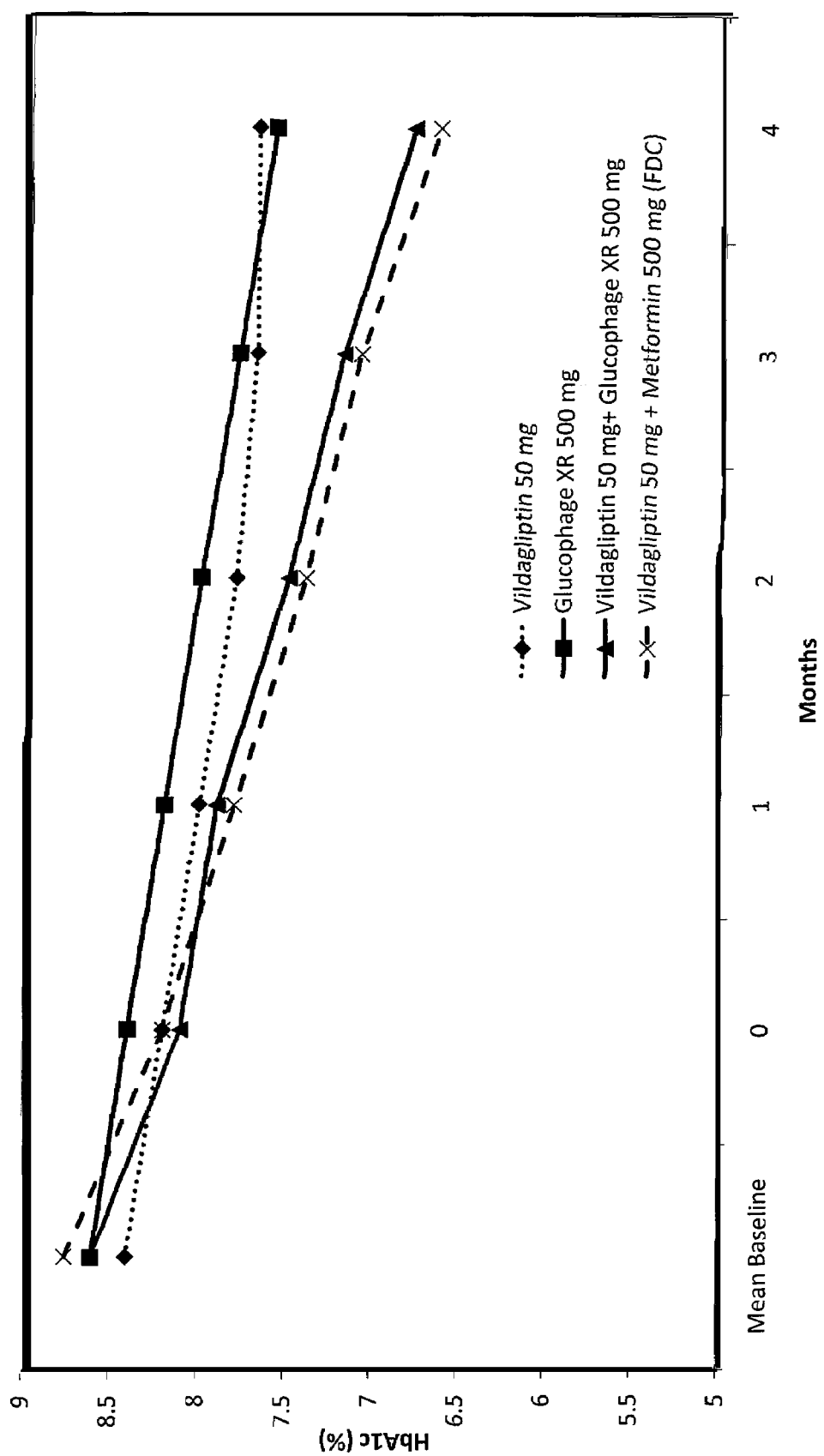
FIG. 12: Illustrates changes in hemoglobin A1c (HbA1c) (+/−.SEM) during administration of 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

FIG. 12: Illustrates changes in hemoglobin A1c (HbA1c) (+/−.SEM) during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

Figure 13:
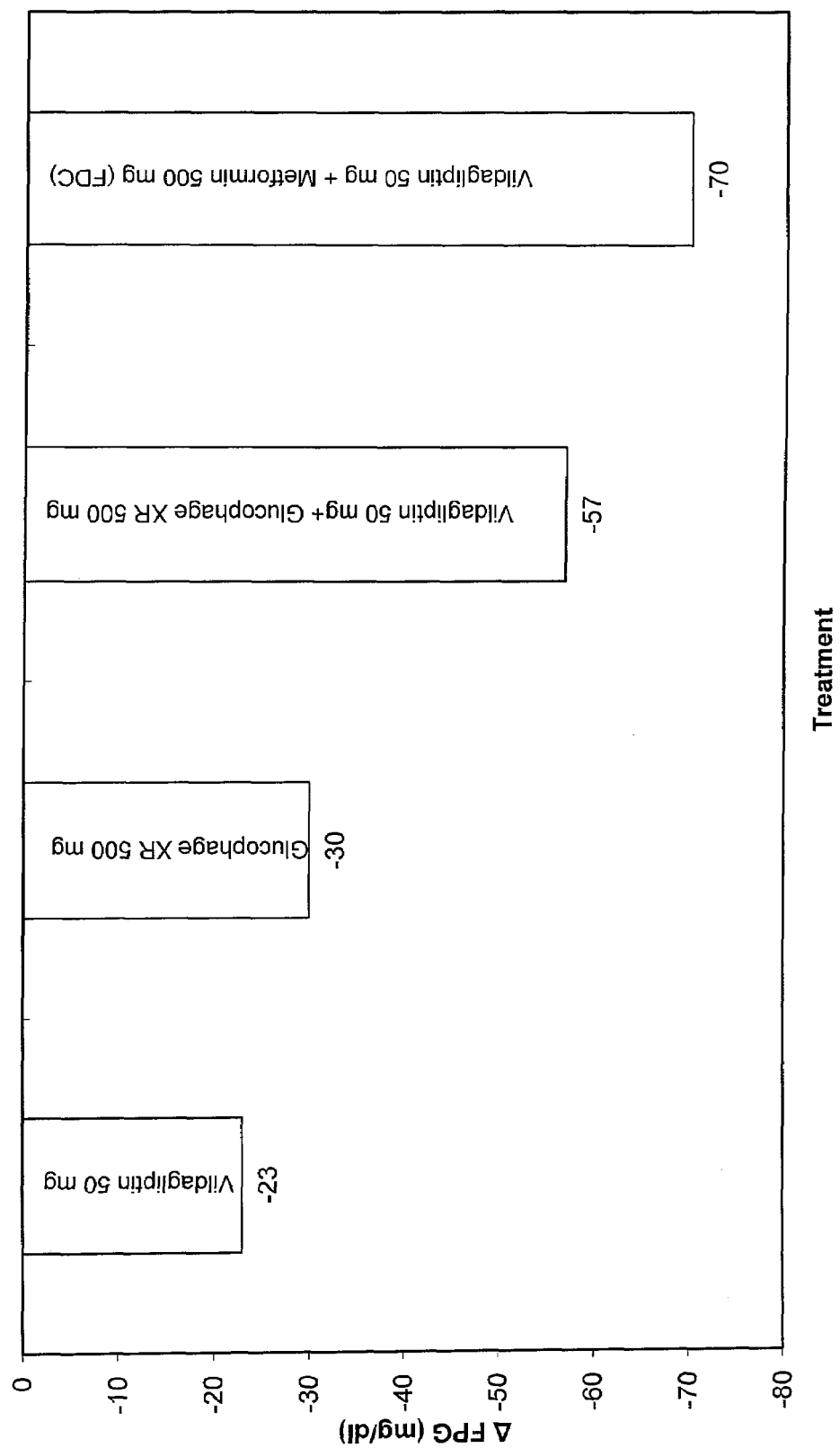
FIG. 13: Illustrates changes in Δ FGP (mg/dl) at 95% CI during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

FIG. 13: Illustrates a change in Δ FGP (mg/dl) at 95% CI during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

Figure 14:
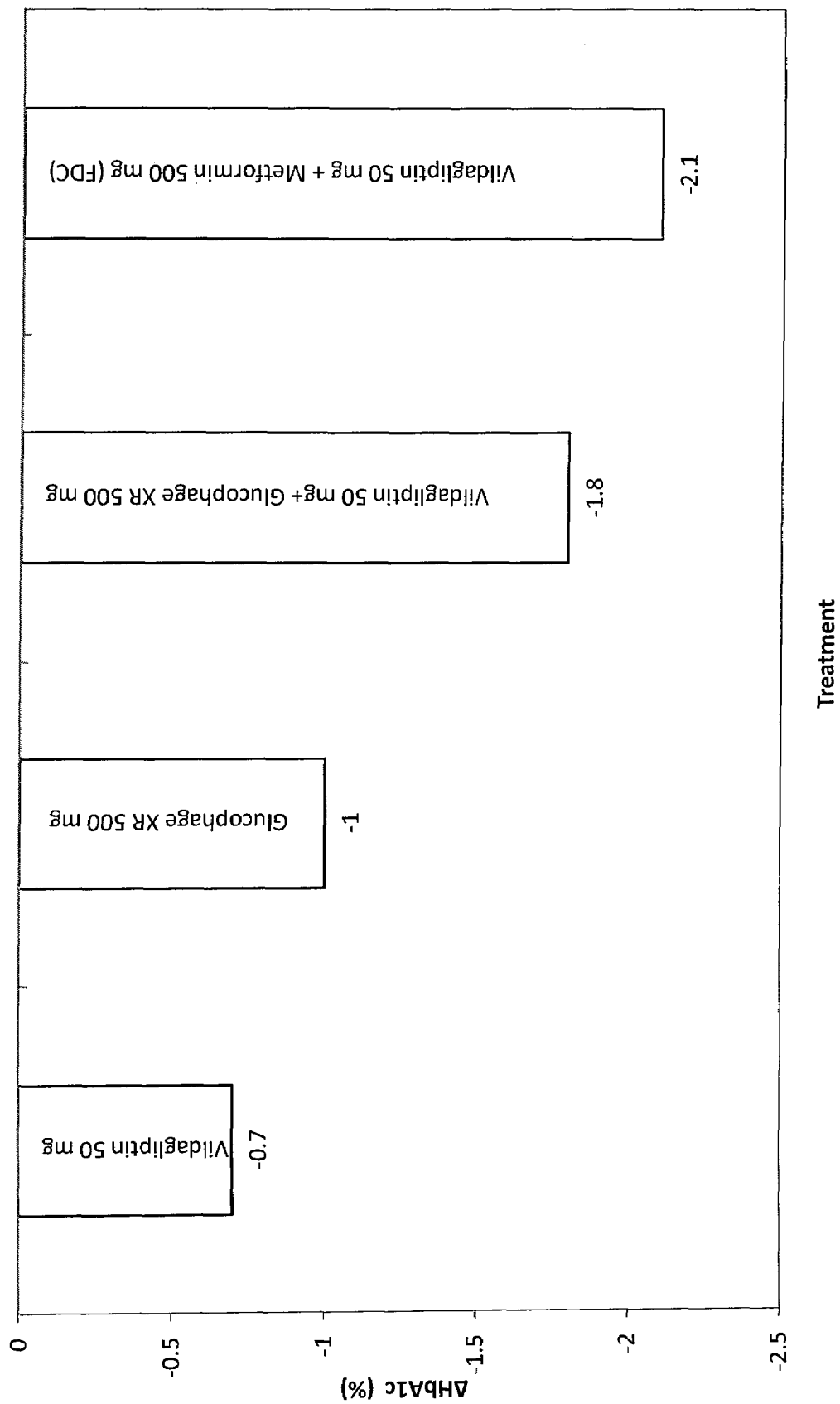
FIG. 14: Illustrates changes Δ HbA1c during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

FIG. 14: Illustrates a change Δ HbA1c during administration of: 1) a fixed dose combination (FDC) of Vildagliptin 50 mg and slow release Metformin 500 mg (Example 3) administered two times daily orally and 2) Co-administration of Vildagliptin 50 mg plus Glucophage XR 500 mg, 3) Glucophage XR 500 mg (2 tablets) and 4) Vildagliptin 50 mg, all formulations administered two times daily orally.

Figure 15:
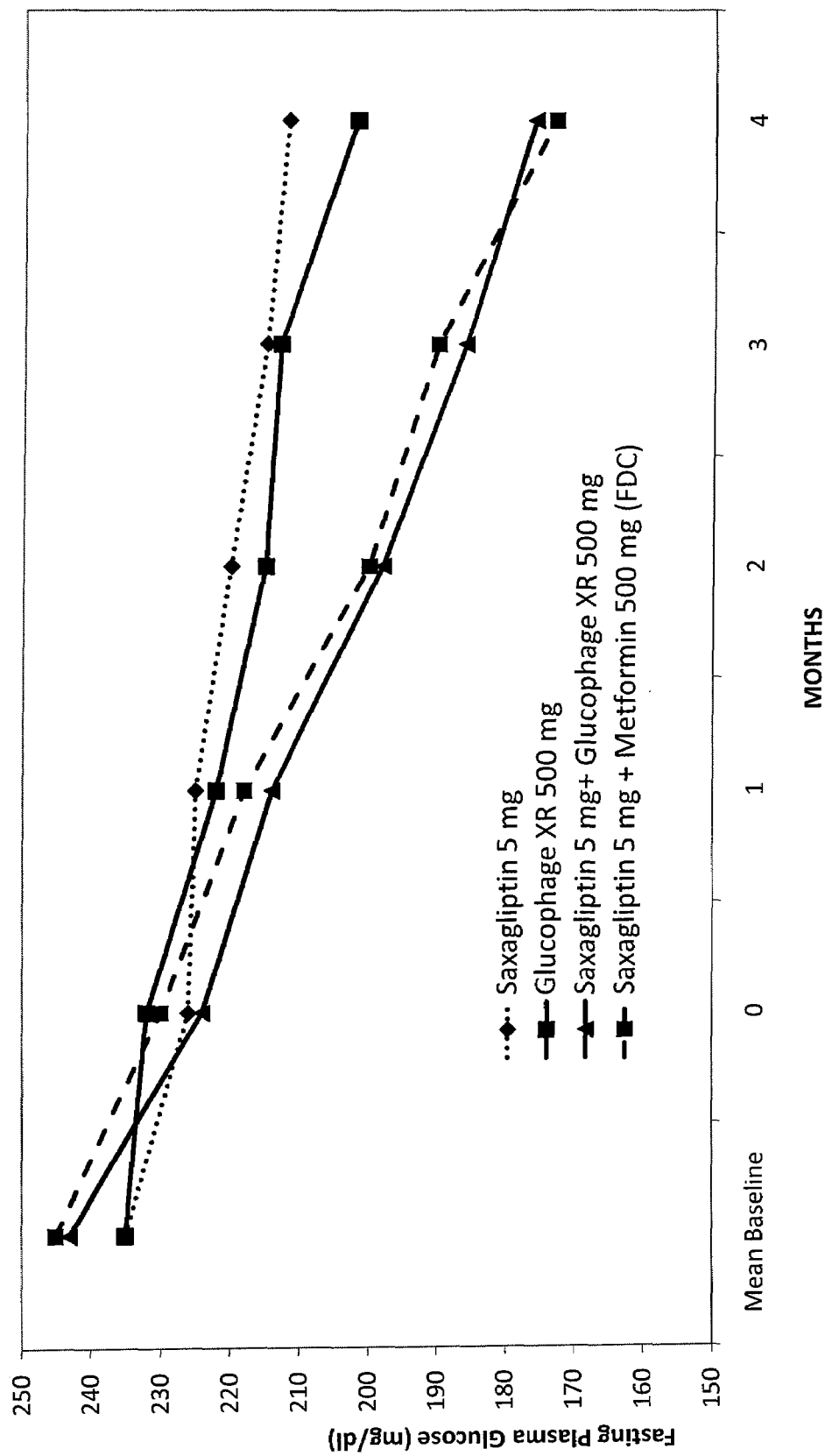
FIG. 15: Illustrates changes in fasting plasma glucose (FPG) (+/−) SEM during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

FIG. 15: Illustrates changes in fasting plasma glucose (FPG) (+/−−) SEM) during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

Figure 16:
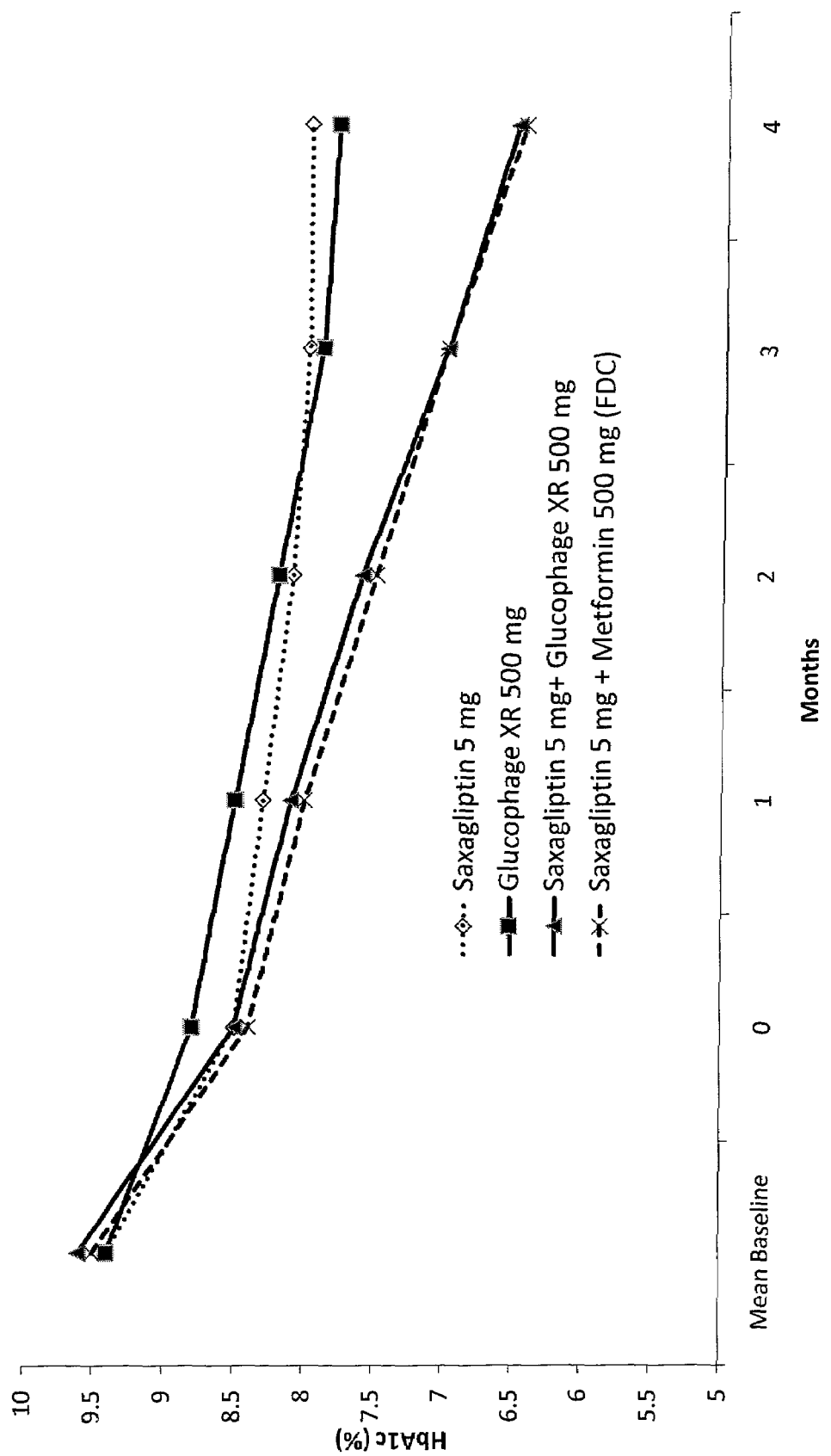
FIG. 16: Illustrates changes in hemoglobin A1c (HbA$_{1c}$) (+/−.SEM) during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

FIG. 16: Illustrates changes in hemoglobin A1c (HbA$_{1c}$) (+/−.SEM) during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

Figure 17:
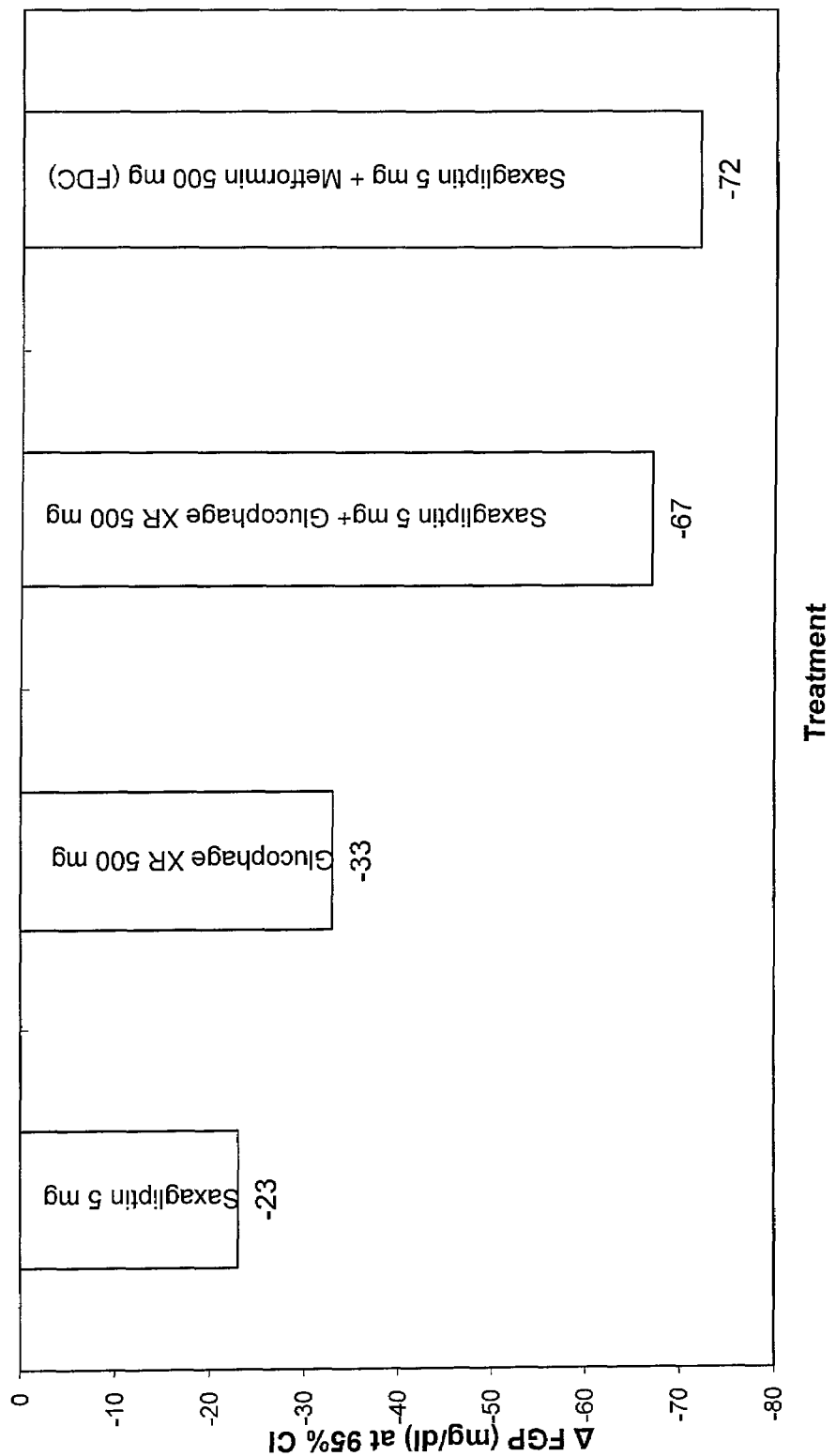
FIG. 17: Illustrates a change in mean Δ FPG during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

FIG. 17: Illustrates a change in mean Δ FPG during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

Figure 18:
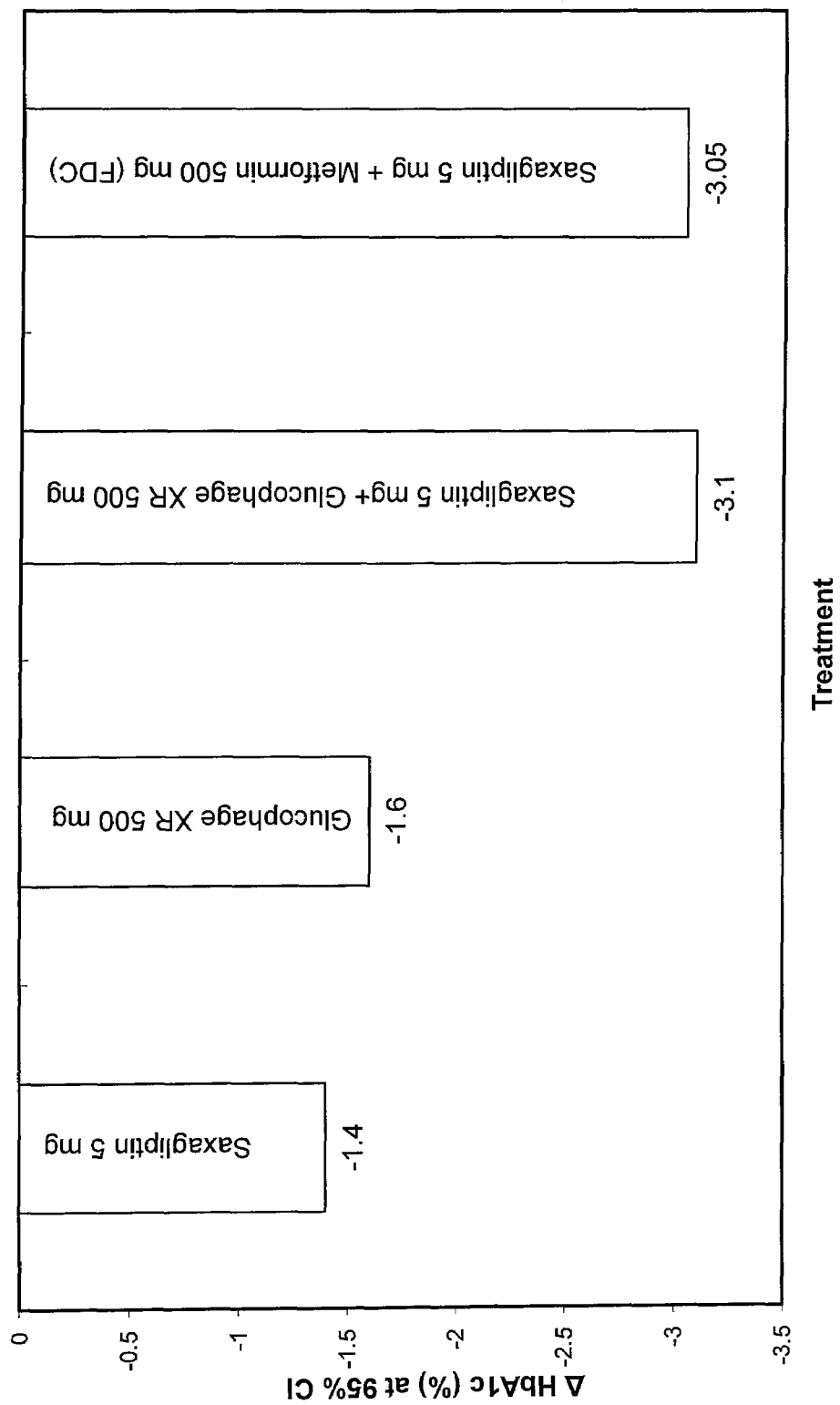
FIG. 18: Illustrates a change in mean Δ HbA1c during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

FIG. 18: Illustrates a change in mean Δ HbA1c during administration of: 1) Co-administration of Saxagliptin 5 mg plus Glucophage XR 500 mg, 2) Fixed dose administration of saxagliptin 5 mg plus slow release metformin 500 mg (Example 4), 3) Glucophage XR 500 mg (2 tablets) and 4) Saxagliptin 5 mg, all formulations administered two times daily orally.

Figure 19:
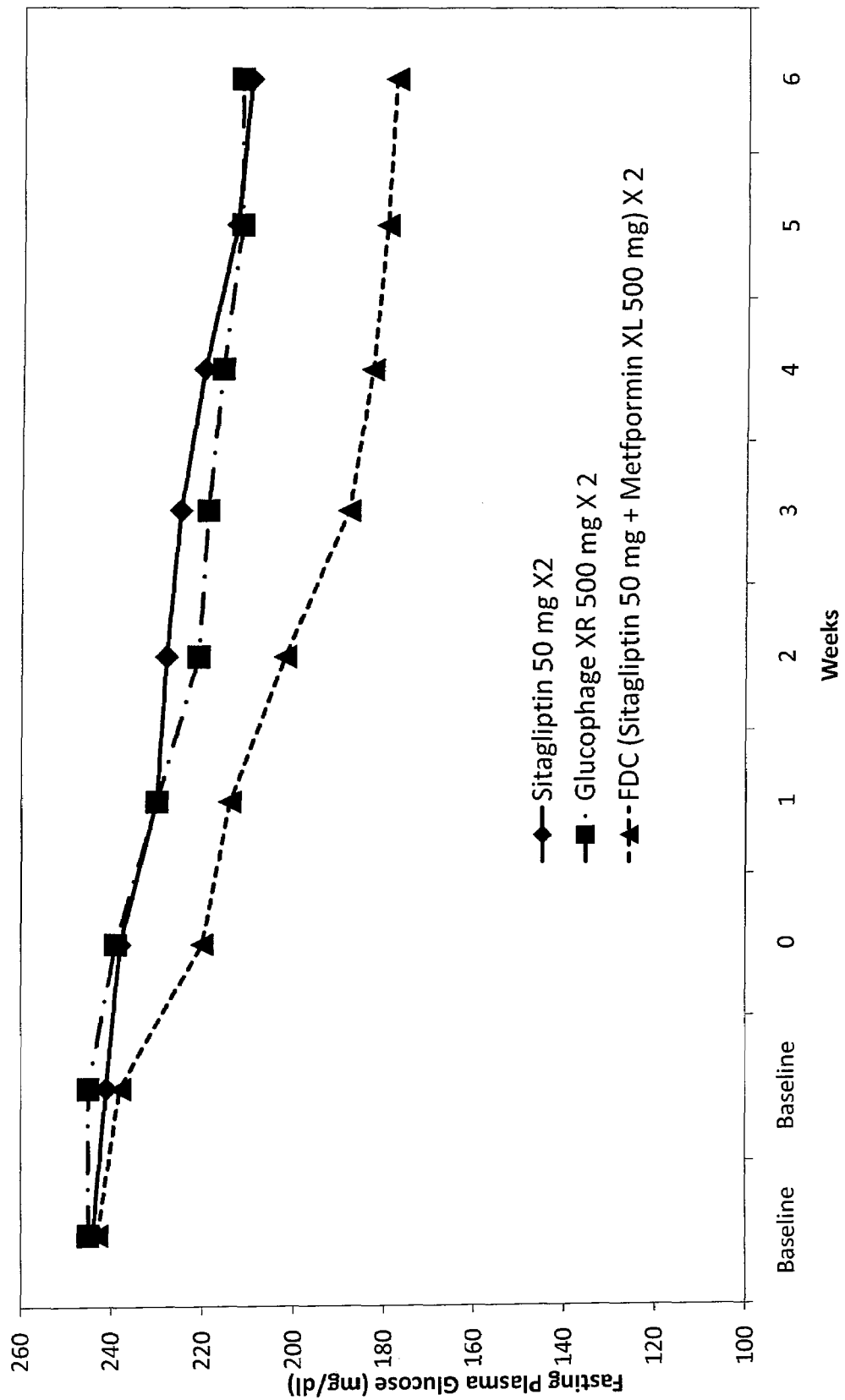
FIG. 19; Illustrates changes in fasting plasma glucose (FPG) (+/−) SEM) during administration of: 1) a fixed dose combination (FDC) of Sitagliptin 50 mg and slow release Metformin 500 mg (Example 1)-Two Tablets, 2) Glucophage XR 500 mg (2 tablets) and 3) Sitagliptin 50 mg (Two Tablets), all drugs administered once daily orally.

FIG. 19; Illustrates changes in fasting plasma glucose (FPG) (+/−−) SEM during administration of: 1) a fixed dose combination (FDC) of Sitagliptin 50 mg and slow release Metformin 500 mg (Example 1)-Two Tablets, 2) Glucophage XR 500 mg (2 tablets) and 3) Sitagliptin 50 mg (Two Tablets), all drugs administered once daily orally.

Figure 20:
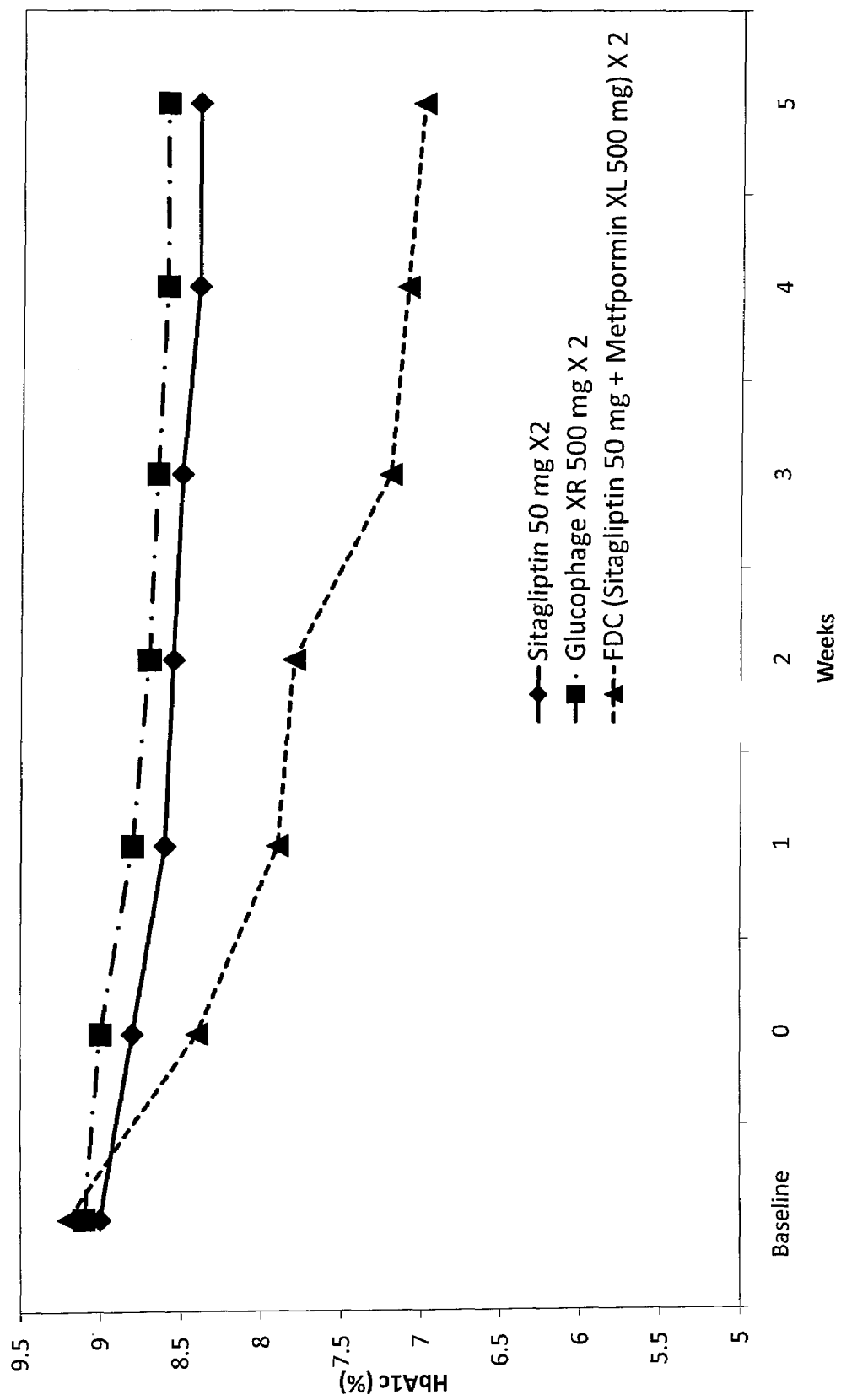
FIG. 20: Illustrates changes in hemoglobin A1c (HbA1c) (+/−.SEM) during administration of: 1) a fixed dose combination (FDC) of Sitagliptin 50 mg and slow release Metformin 500 mg (Example 1)-Two Tablets, 2) Glucophage XR 500 mg (2 tablets) and 3) Sitagliptin 50 mg (Two Tablets), all drugs administered once daily orally.

FIG. 20: Illustrates changes in hemoglobin A1c (HbA1c) (+/−.SEM) during administration of: 1) a fixed dose combination (FDC) of Sitagliptin 50 mg and slow release Metformin 500 mg (Example 1)-Two Tablets, 2) Glucophage XR 500 mg (2 tablets) and 3) Sitagliptin 50 mg (Two Tablets), all drugs administered once daily orally.

Figure 21:
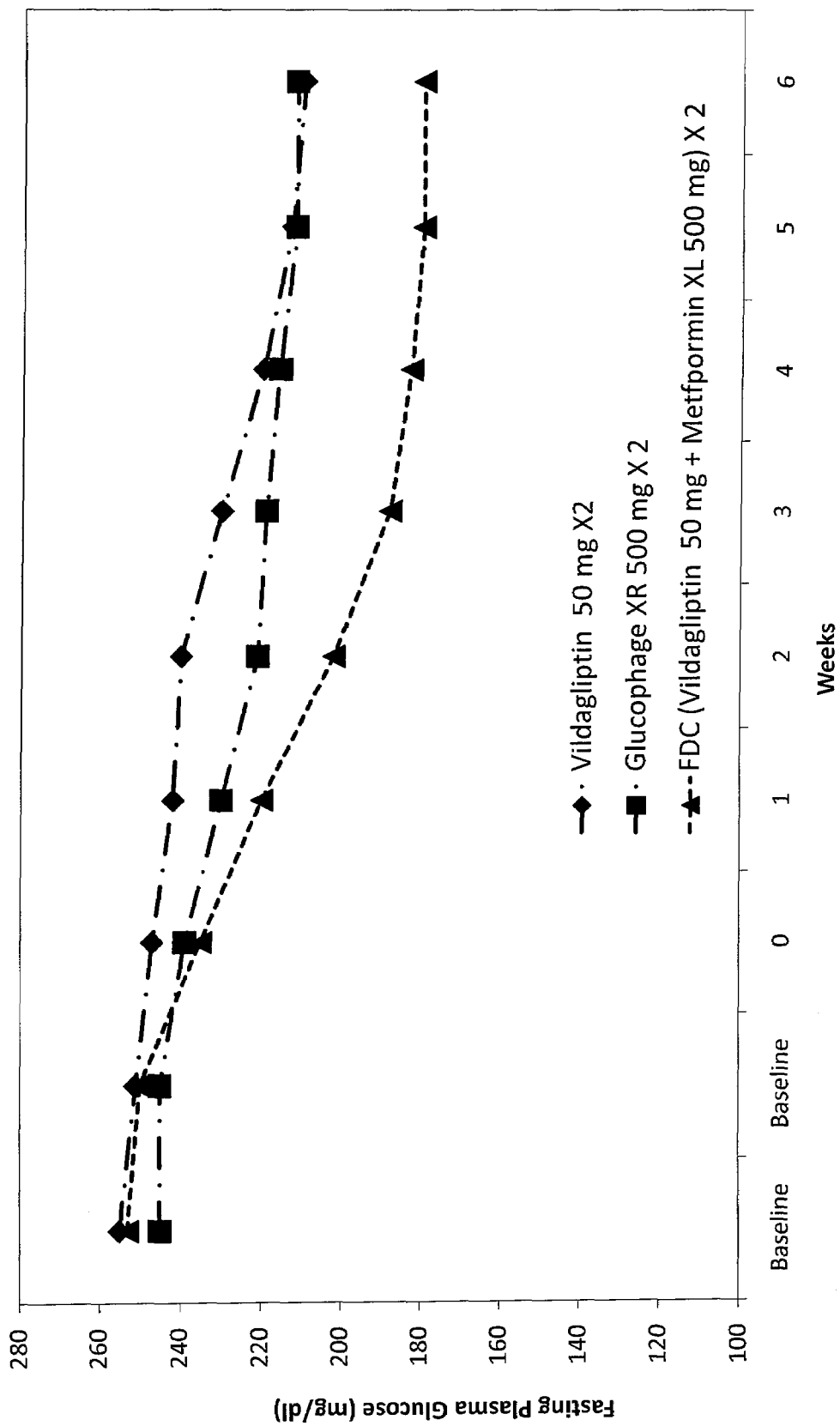
FIG. 21; Illustrates changes in fasting plasma glucose (FPG) (+/−−) SEM) during administration of: 1) a fixed dose combination (FDC) of Vildagliptin 50 and slow release Metformin 500 mg (Example 3)-Two Tablets, 2) Glucophage XR 500 mg (2 tablets) and 3) Vildagliptin 50 mg (Two Tablets), all drugs administered once daily orally.

FIG. 21; Illustrates changes in fasting plasma glucose (FPG) (+/−−) SEM during administration of: 1) a fixed dose combination (FDC) of Vildagliptin 50 and slow release Metformin 500 mg (Example 3)-Two Tablets, 2) Glucophage XR 500 mg (2 tablets) and 3) Vildagliptin 50 mg (Two Tablets), all drugs administered once daily orally.

Figure 22:
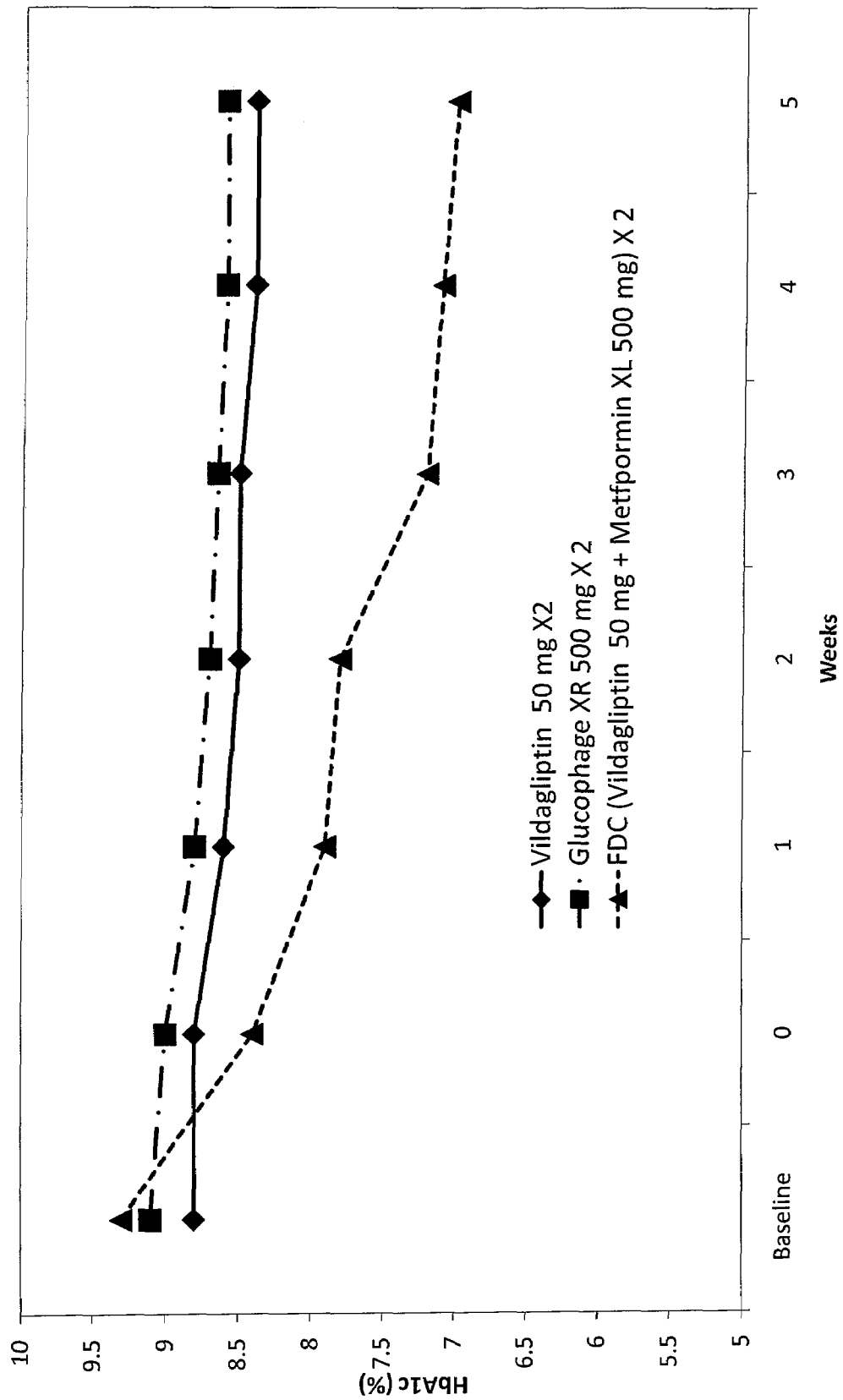
FIG. 22: Illustrates changes in hemoglobin A1c (HbA1c) (+/−.SEM) during administration of: 1) a fixed dose combination (FDC) of Vildagliptin 50 and slow release Metformin 500 mg (Example 3, Two Tablets), 2) Glucophage XR 500 mg (2 tablets) and 3) Vildagliptin 50 mg (Two Tablets), all drugs administered once daily orally.

FIG. 22: Illustrates changes in hemoglobin A1c (HbA1c) (+/−.SEM) during administration of: 1) a fixed dose combination (FDC) of Vildagliptin 50 and slow release Metformin 500 mg (Example 3,Two Tablets), 2) Glucophage XR 500 mg (2 tablets) and 3) Vildagliptin 50 mg (Two Tablets), all drugs administered once daily orally.

Figure 23:
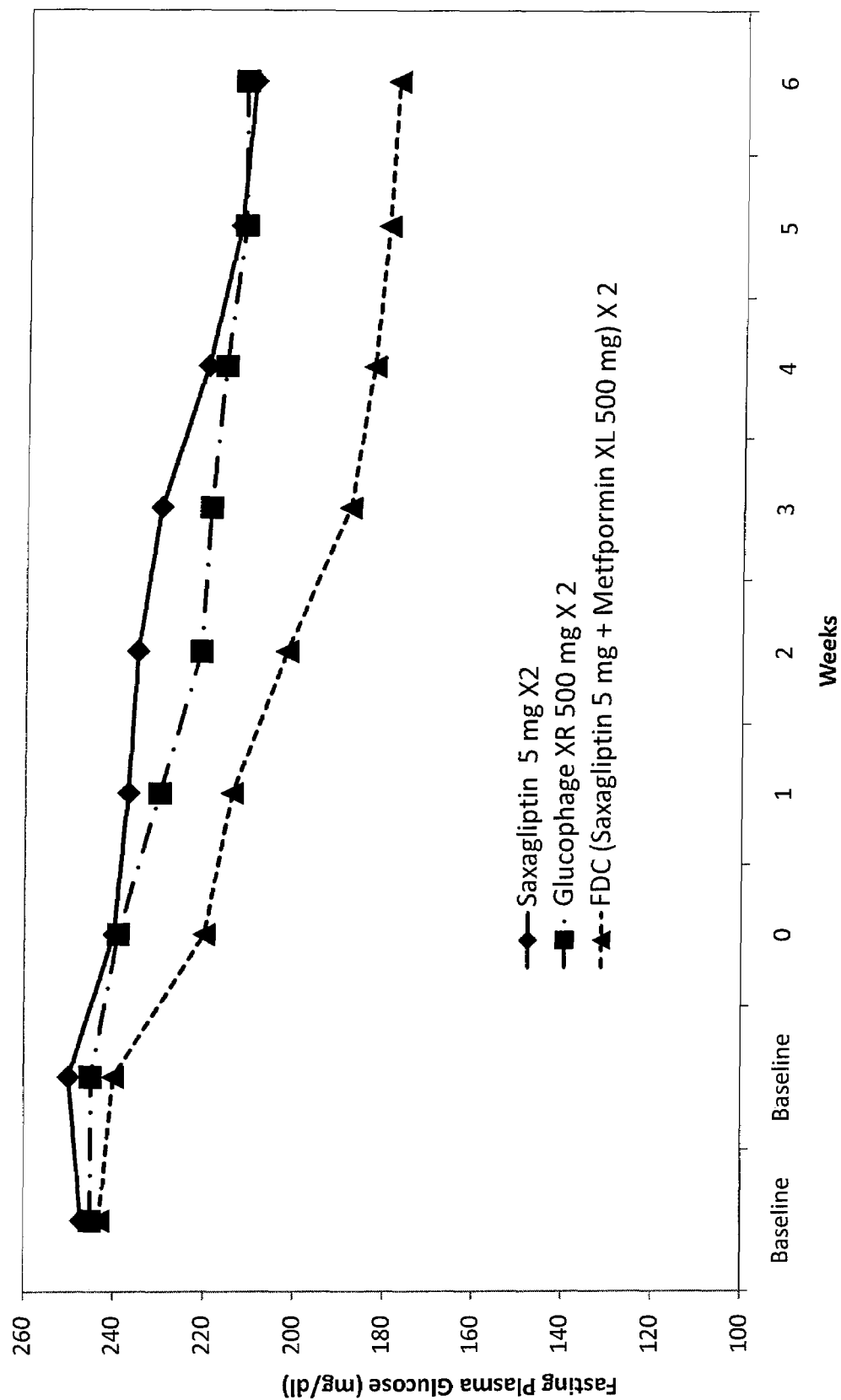
FIG. 23; Illustrates changes in fasting plasma glucose (FPG) (+/−−) SEM) during administration of: 1) a fixed dose combination (FDC) of Saxagliptin 5 mg and slow release Metformin 500 mg (Example 4, Two Tablets), 2) Glucophage XR 500 mg (2 tablets) and 3) Saxagliptin 5 mg (Two Tablets), all drugs administered once daily orally.

FIG. 23; Illustrates changes in fasting plasma glucose (FPG) (+/−−) SEM during administration of: 1) a fixed dose combination (FDC) of Saxagliptin 5 mg and slow release Metformin 500 mg (Example 4, Two Tablets), 2) Glucophage XR 500 mg (2 tablets) and 3) Saxagliptin 5 mg (Two Tablets), all drugs administered once daily orally.

Figure 24:
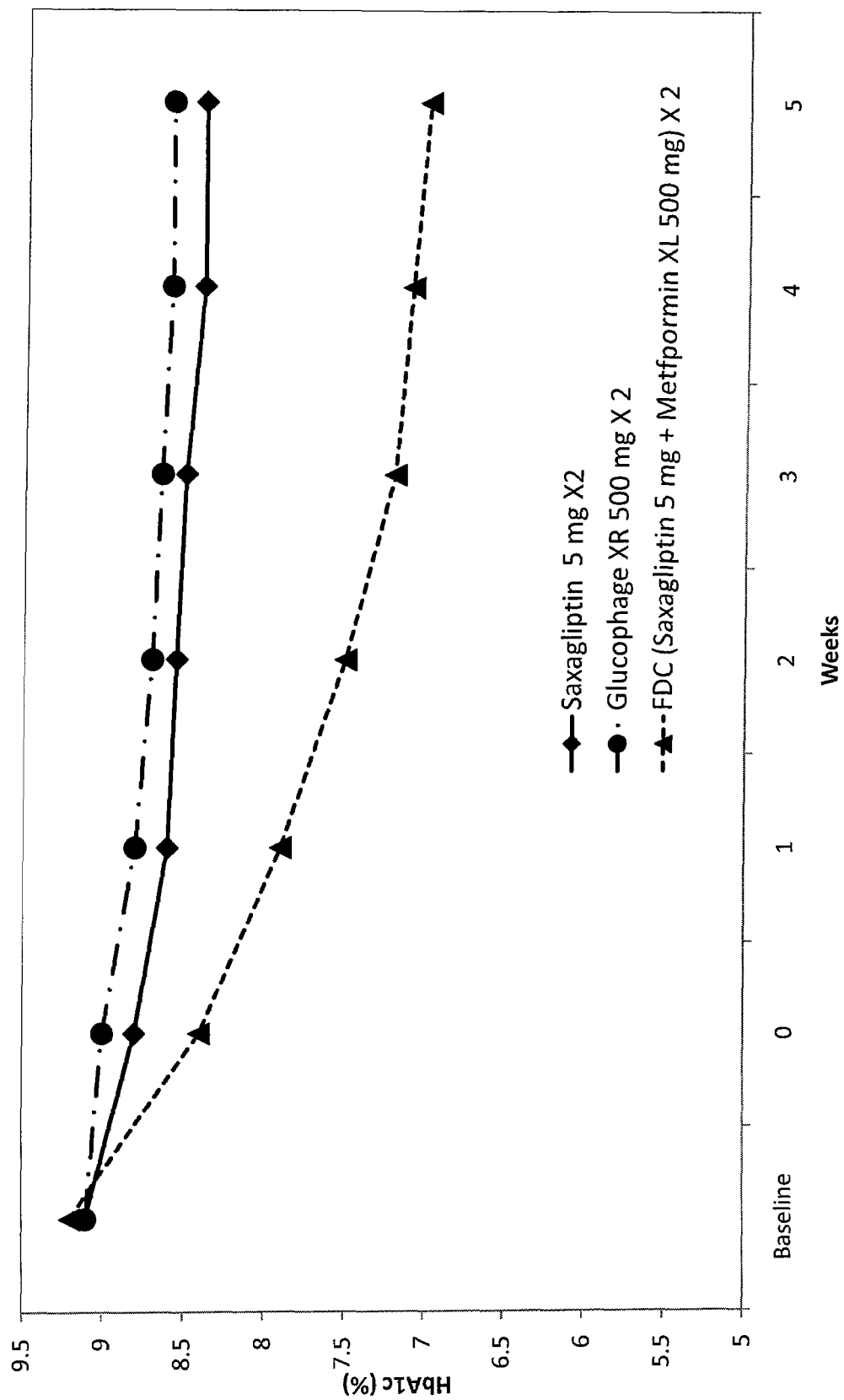
FIG. 24: Illustrates changes in hemoglobin A1c (HbA1c) (+/−.SEM) during administration of: 1) a fixed dose combination (FDC) of Saxagliptin 5 mg and slow release Metformin 500 mg (Example 4, Two Tablets), 2) Glucophage XR 500 mg (2 tablets) and 3) Saxagliptin 5 mg (Two Tablets), all drugs administered once daily orally.

FIG. 24: Changes in hemoglobin A1c (HbA1c) (+/−.SEM) during administration of: 1) a fixed dose combination (FDC) of Saxagliptin 5 mg and slow release Metformin 500 mg (Example 4, Two Tablets), 2) Glucophage XR 500 mg (2 tablets) and 3) Saxagliptin 5 mg (Two Tablets), all drugs administered once daily orally.

8. Conclusions

The data illustrate that an anti-diabetic combination comprising a dipeptidyl peptidase IV inhibitor and a slow release biguanide were effective. The combination therapy of dipeptidyl peptidase IV inhibitor and a slow release biguanide was found to be safe and well-tolerated. In addition, the compositions provided significant therapeutic benefits.

The foregoing study establishes that the combination of a dipeptidyl peptidase IV inhibitor and a slow release biguanide provides a clinically significant and unexpected further lowering of fasting glucose compared to either agent used alone. The changes are significant to conclude that the results are due to synergistic effect of a dipeptidyl peptidase IV inhibitor and the slow release biguanide and rule out the addition effect.

The abbreviations used herein have their conventional meaning within the chemical and biological arts. All publications, patents, and patent documents cited in the specification are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

What is claimed is:

1. A pharmaceutical composition for treating diabetes consisting of:
   a) a slow release core comprising metformin or a pharmaceutically acceptable salt thereof, and optionally one pharmaceutically acceptable excipient, and
   b) an immediate release coating comprising a dipeptidyl peptidase IV inhibitor or a pharmaceutically acceptable salt thereof;

wherein the said composition exhibits a dissolution profile such that after two hours from 0 to about 25 percent of metformin is released, after four hours from about 10 to about 45 percent of metformin is released, after eight hours from about 30 to about 90 percent of metformin is released, after twelve hours not less than 50 percent of metformin is released, and after sixteen hours not less than 60 percent of metformin is released, when tested in a USP type 1 apparatus, at pH 2.0 in a HCl-0.3M KCl buffer solution.

2. The pharmaceutical composition of claim 1, wherein the dipeptidyl peptidase IV inhibitor is Sitagliptin, Vildagliptin, Saxagliptin, Alogliptin, Dutogliptin, GRC-8200, SSR-162369, or a pharmaceutically acceptable salt thereof.

3. The pharmaceutical composition of claim 1, wherein the excipient is an adjuvant, a preservative, an antioxidant, a thickening agent, a chelating agent, an antifungal agent, an antibacterial agent, an isotonic agent, a flavoring agent, a sweetening agent, an anti-foaming agent, a colorant, a diluent, a moistening agent, a parietal cell activator, or combination of thereof.

4. The pharmaceutical composition of claim 1, wherein at least 95% of the dipeptidyl peptidase IV inhibitor is released within 120 minutes when tested in a USP type 1 apparatus, at pH 2.0 in a HCl-0.3M KCl buffer solution.

5. The pharmaceutical composition of claim 4 wherein at least 95% of the dipeptidyl peptidase IV inhibitor is released within 90 minutes when tested in a USP type 1 apparatus, at pH 2.0 in a HCl-0.3M KCl buffer solution.

6. The pharmaceutical composition of claim 1, wherein the dipeptidyl peptidase IV inhibitor is Sitagliptin phosphate.

7. The pharmaceutical composition of claim 1, wherein the dipeptidyl peptidase IV inhibitor is Vildagliptin.

8. The pharmaceutical composition of claim 1, wherein the dipeptidyl peptidase IV inhibitor is saxagliptin.

9. A pharmaceutical kit wherein the kit includes a composition of claim 1 consisting of a dipeptidyl peptidase IV inhibitor or a pharmaceutically acceptable salt thereof and slow release metformin or a pharmaceutically acceptable salt thereof.

10. The pharmaceutical composition of claim 1, wherein the amount of dipeptidyl peptidase IV inhibitor is from about 1 and to about 1000 mg and the amount of metformin is from about 100 to about 2000 mg.

11. The pharmaceutical composition of claim 1, wherein the amount of dipeptidyl peptidase IV inhibitor is from about 50 mg to about 300 mg and the amount of metformin is from about 300 mg to about 2000 mg.

* * * * *